US006934578B2

United States Patent
Ramseth

(12) United States Patent
(10) Patent No.: US 6,934,578 B2
(45) Date of Patent: *Aug. 23, 2005

(54) METHOD AND APPARATUS FOR INTERACTIVE ANNOTATION AND MEASUREMENT OF TIME SERIES DATA WITH AUTOMATIC MARKER SEQUENCING

(75) Inventor: Douglas J. Ramseth, Reno, NV (US)

(73) Assignee: Covance Inc., Princeton, NJ (US)

(*) Notice: Subject to any disclaimer, the term of this patent is extended or adjusted under 35 U.S.C. 154(b) by 364 days.

This patent is subject to a terminal disclaimer.

(21) Appl. No.: 10/246,274

(22) Filed: Sep. 18, 2002

(65) Prior Publication Data

US 2004/0054296 A1 Mar. 18, 2004

(51) Int. Cl.⁷ .............................................. A61B 5/04
(52) U.S. Cl. ........................................................ 600/523
(58) Field of Search ................................. 600/509, 523, 600/524; 607/27; 345/689

(56) References Cited

U.S. PATENT DOCUMENTS

| 4,601,291 A | * | 7/1986 | Boute et al. ................. 607/27 |
| 5,305,202 A | * | 4/1994 | Gallant et al. ............. 600/524 |
| 5,469,858 A | * | 11/1995 | Osborne ..................... 600/523 |
| 6,708,057 B2 | | 3/2004 | Morganroth |

* cited by examiner

Primary Examiner—George Manuel
(74) Attorney, Agent, or Firm—McDermott Will & Emery LLP

(57) ABSTRACT

A system displays time-series data, such as electrocardiographic data. The data may be displayed as a trace with markers identifying data features. The markers may be automatically sequenced by the system.

35 Claims, 18 Drawing Sheets

METHOD AND APPARATUS FOR INTERACTIVE ANNOTATION AND MEASUREMENT OF TIME SERIES DATA WITH AUTOMATIC MARKER SEQUENCING

FIELD OF THE INVENTION

The invention relates to display systems and, more particularly, to interactive displays for the presentation, annotation, and analysis of the features of electrocardiogram waveforms and other time series data.

BACKGROUND OF THE INVENTION

A number of interactive display devices have been developed to provide immediate visual feedback to a user of a computer, or other electronic or electromechanical equipment, and to thereby allow the user to precisely control operations related to the display. The movement of a cursor on a display, for example, permits the user to insert words within text as the user types a document. Similarly, by activating a slide bar at one side of the display, the user can scroll through the document much more rapidly. Pull-down and pop-up menus permit the user to activate other functions, such as saving or printing a document, checking the spelling of a document, etc. The display is interactive in the sense that signals from an input device, such as a keyboard, a mouse, touch-pad, touch-screen, or voice input system, is reflected in the modification of the display and in an underlying modification of data related to the display. That is, for example, not only is the cursor moved on the screen in response to input from the mouse, the underlying document, stored in electronic form within the computer, also reflects the cursor movement.

The real-time display provided by endoscopic instruments during surgery allows a surgeon to precisely control the position, direction, and speed of surgical tools in the process of delicate brain surgery that would otherwise be impossible. Although the tool might be positioned physically by powerful magnets, for example, control of the magnets and ultimately of the surgical tools, is in the hands of a surgeon. The surgeon may rely upon a display to provide him with immediate visual feedback via a live video feed while he employs a joystick or other input device to control the surgical tool. The surgeon may be operating by "dead reckoning" in that the only feedback he may be receiving is from the video feed and from some sort of an indicator which reveals the position of the tool within the patient, without revealing anything about the tool itself, that is, any changes in the cross-section of the tool, for example.

Interactive display devices are also used in the analysis of complex data sets. Insight may be gained by viewing the data in a unique manner that permits the visual correlation of data. Just as Linneaus' binomial organization of biological specimens into species and genus provided an organizational framework for understanding the vast diversity of the biosphere, an opportune display of data or of the results of operations performed on the data, may allow a user to gain insights that might otherwise be overlooked.

Although current interactive displays provide adequate feedback for many applications, there is a need for an interactive display which provides visual feedback to a user for operations that are more complex than simply positioning a cursor within a field of text. In particular, the display and on-screen measurement of time series data, such as electrocardiogram data, would be highly desirable.

SUMMARY

An interactive display system in accordance with the principles of the invention includes an input device, a controller, and a display. The controller is configured to display time-series data, such as electrocardiogram data, in graphical form, on the display. The controller is also configured to position one or more markers on the display, as dictated by user input received through an input device, and to correlate the underlying data to the point(s) indicated by the marker position.

The controller may be responsive to signals from the input device by modifying the size, shape, position, or other aspects of the marker. Such modifications to the marker are provided as a visual feedback mechanism for a user. In addition to the marker modification, the controller may operate on data, or provide an indication to another controller that the data should be operated upon, in a predetermined manner corresponding to the manipulation of the marker. For example, a time interval may be marked off by the manipulation of one or more markers, and the controller may respond, not only by positioning the markers according to user input, but also by computing the time and/or other values (e.g., average signal level over the interval). Additionally, modifications to the position of the marker may be reflected by modifications to information displayed, with, for example, the coordinates of one or more markers displayed and updated "on the fly" as a marker is repositioned on the display. The coordinates may represent a multi-dimensional space in which dimensions are devoted to signal level, time, event number, or other variables, for example. Markers may be combined with other interactive display devices and techniques such as pulldown or popup menus, or sliders, for example.

In an illustrative embodiment, the interactive display presents electrocardiogram data in a manner that emulates the standard paper recording format. For example, data from a standard ECG recording may be displayed as traces overlaid on a millimeter grid reference background. By displaying ECG data in much the same format as that of a conventional ECG paper printout, the system capitalizes on the pattern recognition skills developed by cardiologists through years of training and experience. Moreover, the interactive display system maintains the aspect ratio, thereby preserving the pattern-recognition advantages, during electronic magnification (zoom) operations. By preserving the aspect ratio in this manner, doubling, for example, both the horizontal and vertical scales for both the ECG waveform and the reference grid for a 2× magnified view of an ECG, a cardiologist may make precise, highly-refined ECG measurements, even while viewing an undistorted representation of the ECG.

A user may select one or more features of interest by manipulating one or more markers. Each marker may be a conventional marker, such as a cursor such as is used in word-processing applications, for example. Alternately, a marker may be a vertical line that intersects the waveform and has an associated alphanumeric character, such as a "P" (corresponding to atrial depolarization) to identify the meaning of the marked point. The marker may also be conic, such as a graphic corresponding to a frontal plane QRS axis, for example. Intervals, such as PR, QRS, QT, and RR intervals, may be measured on-screen using one or more markers. That is, for example, a user may employ a single marker to indicate a point for which measurements, such as voltage and time, are desired. The user may use a single marker to set the beginning of an interval for which measurements are desired, then place a marker at the end of the desired interval, or a plurality of markers may be employed to denote data values or data intervals of interest.

Multiple markers may also be employed, with one assigned to mark the beginning of an interval and one assigned to mark the end of an interval of interest, for example. The interactive display system also provides for "automatic" marking. For example, in one mode of operation a user may mark the QRS onset feature on a trace of interest in response to which the system completes the markings for the P (P onset), J (QRS end), and T (T wave end) points and computes the intervals associated with this beat. Measurements may be displayed in close proximity to the measurement marks, overlaid on the strip chart background, and/or may be displayed in one or more separate "reporting areas on the display. The displayed measurements may be updated continuously, so that, as a marker is moved across the strip chart background, the measurement display continuously changes to reflect the updated position of the marker. Alternatively, the displayed measurements may be updated upon finalization of a marker position. The finalization may be effected through use of an "enter" keystroke, for example.

The time-series data may be obtained directly from an electrocardiogram machine that provides digital output. If the electrocardiogram machine provides only analog output, the analog signal(s) may be converted to digital form for processing by an interactive display in accordance with the principles of the present invention. Whether the analog ECG signals are converted to digital form by the ECG machine or in post-processing, a user may process the corresponding digital data on the interactive display directly from the ECG machine or from stored ECG data. Additionally, one or more users may use an interactive display in accordance with the principles of the present invention to process ECG data that is obtained at one or more patient sites and transmitted, via a telecommunications network, for example, to an ECG analysis center. Digitized ECG data may be transmitted to an analysis center and stored for future processing or placed in a queue for immediate processing. Alarms of varying degrees of urgency may be activated by an interactive display in accordance with the principles of the present invention in response to ECG data analyses.

BRIEF DESCRIPTION OF THE DRAWINGS

The above and further features, aspects, and advantages of the invention will be apparent to those skilled in the art from the following detailed description, taken together with the accompanying drawings in which.

DETAILED DESCRIPTION

Figure 1:
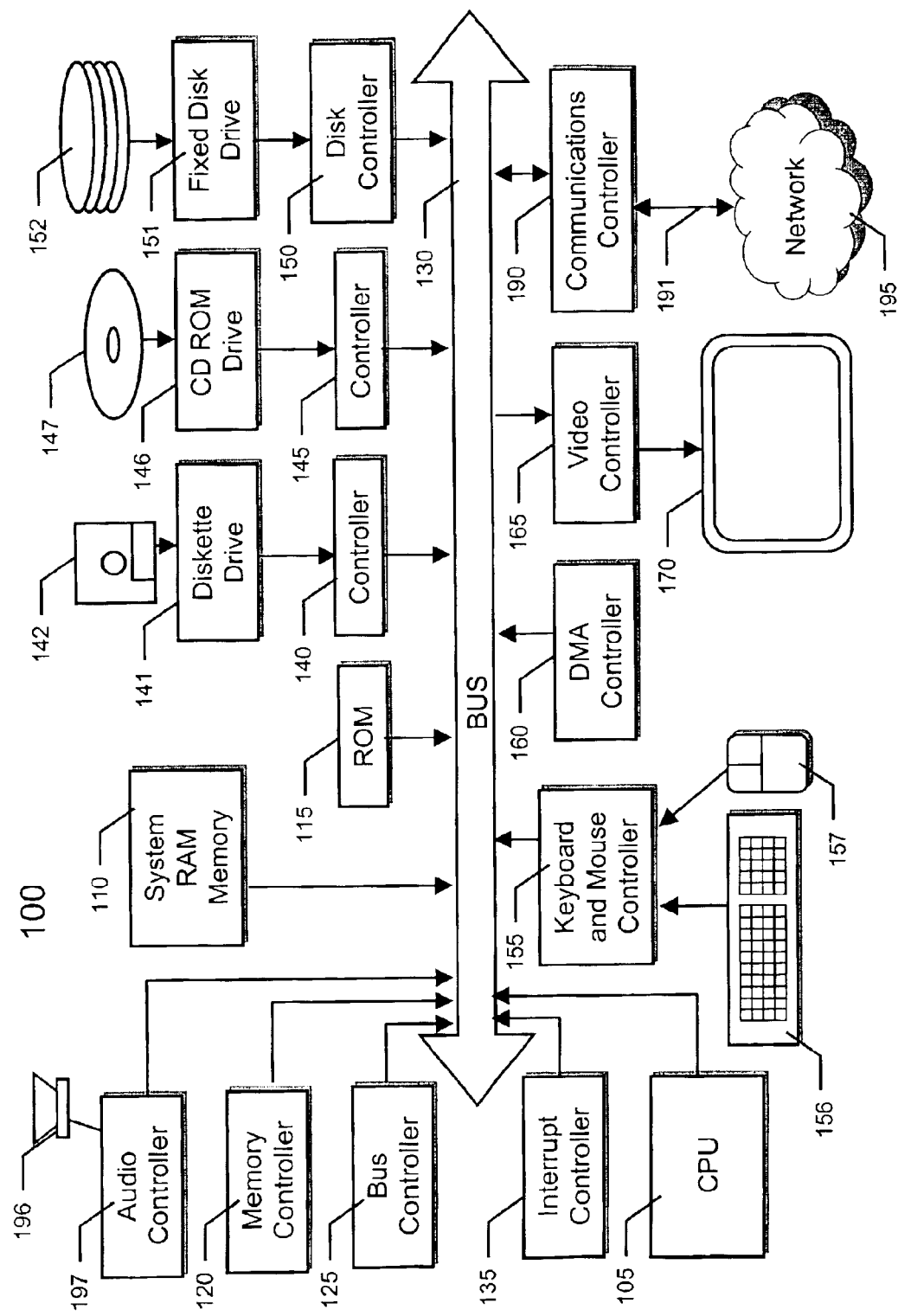
FIG. 1 is a conceptual block diagram of a system that may employ an interactive display in accordance with the principles of the invention.

FIG. 1 illustrates the system architecture for a computer system 100 on which the invention may be implemented. The exemplary computer system of FIG. 1 is for descriptive purposes only. Although the description may refer to terms commonly used in describing particular computer systems, the description and concepts equally apply to other systems, including systems having architectures dissimilar to FIG. 1.

Computer system 100 includes a central processing unit (CPU) 105, which may be implemented with a conventional microprocessor, a random access memory (RAM) 110 for temporary storage of information, and a read only memory (ROM) 115 for permanent storage of information. A memory controller 120 is provided for controlling RAM 110.

A bus 130 interconnects the components of computer system 100. A bus controller 125 is provided for controlling bus 130. An interrupt controller 135 is used for receiving and processing various interrupt signals from the system components.

Mass storage may be provided by diskette 142, CD ROM 147, or hard drive 152. Data and software may be exchanged with computer system 100 via removable media such as diskette 142 and CD ROM 147. Diskette 142 is insertable into diskette drive 141 which is, in turn, connected to bus 130 by a controller 140. Similarly, CD ROM 147 is insertable into CD ROM drive 146 which is, in turn, connected to bus 130 by controller 145. Hard disc 152 is part of a fixed disc drive 151 which is connected to bus 130 by controller 150.

User input to computer system 100 may be provided by a number of devices. For example, a keyboard 156 and mouse 157 are connected to bus 130 by controller 155. An audio transducer 196, which may act as both a microphone and a speaker, is connected to bus 130 by audio controller 197, as illustrated. It will be obvious to those reasonably skilled in the art that other input devices, such as a pen and/or tabloid may be connected to bus 130 and an appropriate controller and software, as required. DMA controller 160 is provided for performing direct memory access to RAM 110. A visual display is generated by video controller 165 which controls video display 170. Computer system 100 also includes a communications adaptor 190 which allows the system to be interconnected to a local area network (LAN) or a wide area network (WAN), schematically illustrated by bus 191 and network 195. An input interface 199 operates in conjunction with an input device 193 to permit a user to send information, whether command and control, data, or other types of information, to the system 100. The input device and interface may be any of a number of common interface devices, such as a joystick, a touch-pad, a touch-screen, a speech-recognition device, or other known input device.

Operation of computer system 100 is generally controlled and coordinated by operating system software. The operating system controls allocation of system resources and performs tasks such as processing scheduling, memory management, networking, and I/O services, among things. In particular, an operating system resident in system memory and running on CPU 105 coordinates the operation of the other elements of computer system 100. The present invention may be implemented with any number of commercially available operating systems including Windows, OS/2, UNIX and DOS, etc. One or more applications may also run on the CPU 105. If the operating system is a true multitasking operating system, multiple applications may execute simultaneously.

As will be understood by those skilled in the art, Object-Oriented Programming (OOP) techniques involve the definition, creation, use and destruction of "objects". These objects are software entities comprising data elements, or attributes, and methods, or functions, which manipulate the data elements. The attributes and related methods are treated by the software as an entity and can be created, used and deleted as if they were a single item. Together, the attributes and methods enable objects to model virtually any real-world entity in terms of its characteristics, which can be represented by the data elements, and its behavior, which can be represented by its data manipulation functions. In this way, objects can model concrete things like people and computers, and they can also model abstract concepts like numbers or geometrical designs.

Objects are defined by creating "classes" which are not objects themselves, but which act as templates that instruct the compiler how to construct the actual object. A class may, for example, specify the number and type of data variables and the steps involved in the methods which manipulate the data. When an object-oriented program is compiled, the class code is compiled into the program, but no objects exist. Therefore, none of the variables or data structures in the compiled program exist or have any memory allotted to them. An object is actually created by the program at runtime by means of a special function called a constructor which uses the corresponding class definition and additional information, such as arguments provided during object creation, to construct the object. Likewise, objects are destroyed by a special function called a destructor. Objects may be used by using their data and invoking their functions. When an object is created at runtime memory is allotted and data structures are created.

The principle benefits of object-oriented programming techniques arise out of three basic principles; encapsulation, polymorphism and inheritance. More specifically, objects can be designed to hide, or encapsulate, all, or a portion of, the internal data structure and the internal functions. More particularly, during program design, a program developer can define objects in which all or some of the attributes and all or some of the related functions are considered "private" or for use only by the object itself. Other data or functions can be declared "public" or available for use by other programs. Access to the private variables by other programs can be controlled by defining public functions for an object which access the object's private data. The public functions form a controlled and consistent interface between the private data and the "outside" world. Any attempt to write program code which directly accesses the private variables causes the compiler to generate an error during program compilation which error stops the compilation process and prevents the program from being run.

Polymorphism is a concept which allows objects and functions which have the same overall format, but which work with different data, to function differently in order to produce consistent results. For example, an addition function may be defined as variable A plus variable B (A+B) and this same format can be used whether the A and B are numbers, characters or dollars and cents. However, the actual program code which performs the addition may differ widely depending on the type of variables that comprise A and B. Polymorphism allows three separate function definitions to be written, one for each type of variable (numbers, characters and dollars). After the functions have been defined, a program can later refer to the addition function by its common format (A+B) and, at runtime, the program will determine which of the three functions is actually called by examining the variable types. Polymorphism allows similar functions which produce analogous results to be "grouped" in the program source code to produce a more logical and clear program flow.

The third principle which underlies object-oriented programming is inheritance, which allows program developers to easily reuse pre-existing programs and to avoid creating software from scratch. The principle of inheritance allows a software developer to declare classes (and the objects which are later created from them) as related. Specifically, classes may be designated as subclasses of other base classes. A subclass "inherits" and has access to all of the public functions of its base classes just as if these function appeared in the subclass. Alternatively, a subclass can override some or all of its inherited functions or may modify some or all of its inherited functions merely by defining a new function with the same form (overriding or modification does not alter the function in the base class, but merely modifies the use of the function in the subclass). The creation of a new subclass which has some of the functionality (with selective modification) of another class allows software developers to easily customize existing code to meet their particular needs.

Figure 2:
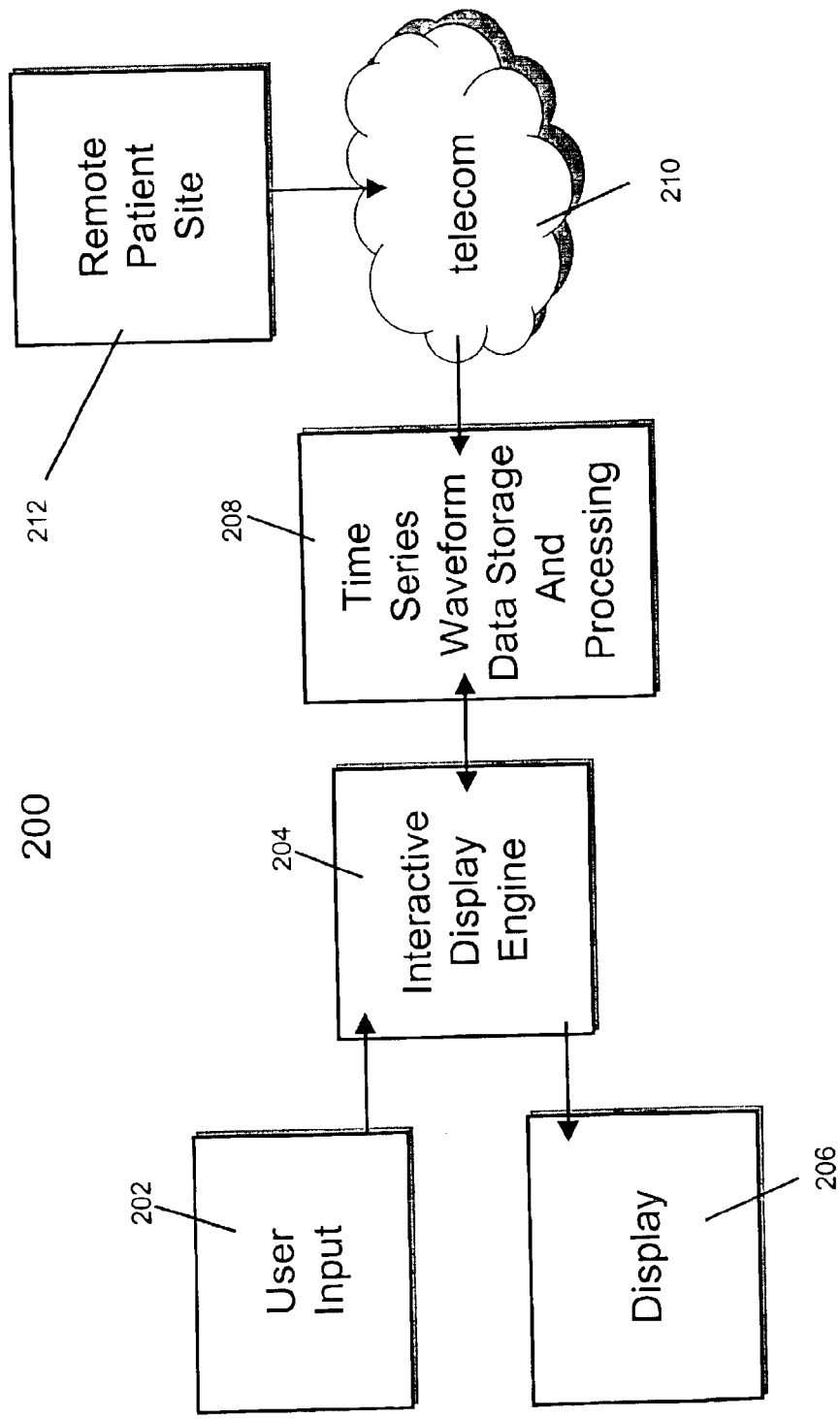
FIG. 2 is a conceptual block diagram of a system that may employ a remote data collection process through a telecommunications network in accordance with the principles of the invention.

FIG. 2 illustrates conceptually the main components of an interactive display system 200 in accordance with the present invention. A user input device 202 may take the form of a known user input device and device interface, such as keyboard and mouse (with corresponding controllers), a joystick, touch pad, touch screen, voice input device, etc. in combination with controllers that may be embodied as various instantiations of object classes. The new interactive display engine 204 may include various ones of the hardware components described in the discussion related to FIG. 1. The interactive display engine 204 is configured to display time-series data, such as electrocardiogram (ECG) data, in graphical form, on the display 206. In one aspect of an interactive display in accordance with the principles of the present invention, electrocardiograms are displayed using a format that is the same as, or substantially similar to, standard paper recording formats. For example, data from a standard ECG recording may be displayed as traces overlaid on a millimeter grid reference background. By displaying ECG data in much the same format as that of a conventional ECG paper printout, the system capitalizes on the pattern recognition skills developed by cardiologists through years of training and experience. Moreover, the interactive display system maintains the aspect ratio, thereby preserving the pattern-recognition advantages, during electronic magnification (zoom) operations. By preserving the aspect ratio in this manner, doubling, for example, both the horizontal and vertical scales for both the ECG waveform and the reference grid for a 2× magnified view of an ECG, a cardiologist may make precise, highly-refined ECG measurements, even while viewing an undistorted representation of the ECG.

The interactive display engine 204 accepts input from the user input device 202. In response to the user input, the system produces output for the display 206 and, depending upon the user input, may record the user input. For example, if the user selects a marker and positions it on the display, the display engine 204 repositions the marker on the display. If the user also selects the marker position, by activating an "enter" key on a keyboard or "double-clicking" a mouse-button, for example the display engine 204 also records the position selected by the user. The engine 204 may also correlate, by computation for example, the underlying data values associated with the selected screen position, then store the screen position, underlying data, and other values. An illustrative object-oriented embodiment of the interactive display engine includes object classes that: read data into onscreen measurements, provide file interfaces, provide standard interfaces to different ECG source types, provide standard interfaces to waveforms, provide forms that allow the selection of interpretive codes for inclusion in a code and comment segment of the report form, to pass a modified ECG to another stage in a review process, to provide display and calculation options, to display report file text and measurements from on-screen analysis and to add assessment codes and/or comments, and to select an ECG file from disk storage.

A time series medical data source 208 may take the form of digitized ECGs stored in computer files, data obtained locally from a subject, or ECGs obtained through a telecommunications link 210 from one or more remote patient locations 212, for example. ECGs obtained through a telecommunications link 210 may be stored locally and processed in prioritized order, as will be described in the discussion related to FIG. 12, for example. In an illustrative embodiment, the interactive display engine 204 presents electrocardiogram data in a manner that is substantially the same as one of the standard paper recording formats. For example, data from a 12 lead resting ECG may be displayed as waveform traces overlaid on a millimeter grid background. By displaying ECG data in much the same format as that of a conventional ECG paper printout, the system capitalizes on the pattern recognition skills developed by cardiologists through years of training and experience. When the interactive display is used to make on-screen measurements, the traces may be "magnified" in a number of different formats, including one in which the aspect ratio of the displayed ECG is maintained. This permits the interactive display to preserve the pattern-recognition advantages of the display, while providing for more accurate placement of markers and a concomitant improvement in the precision of on-screen measurements. By preserving the aspect ratio in this manner, doubling, for example, both the horizontal and vertical ECG scales for a 2× magnified view of an ECG, a cardiologist may make precise, highly-refined ECG measurements, even while viewing an undistorted representation of the ECG.

The time-series data source 208 may be obtained directly from an electrocardiogram machine that provides digital output. If the electrocardiogram machine provides only analog output, the analog signal(s) may be converted to digital form for processing by an interactive display in accordance with the principles of the present invention. Whether the analog ECG signals are converted to digital form by the ECG machine or in post-processing, a user may process the corresponding digital data on the interactive display directly from the ECG machine or from stored ECG data. Additionally, one or more users may use an interactive display in accordance with the principles of the present invention to process ECG data that is obtained at one or more patient sites and transmitted, via a telecommunications network, for example, to an ECG analysis center. Digitized ECG data may be transmitted to an analysis center and stored for future processing or placed in a queue for immediate processing. Alarms of varying degrees of urgency may be activated by an interactive display in accordance with the principles of the present invention in response to ECG data analyses.

In various centralized embodiments of time series medical data analysis systems in accordance with the principles of the present invention, analysis and/or markup of time series medical data may be performed at a centralized location, with data supplied to the centralized location through a telecommunications network 210, for example. The display engine 204 may be responsive to signals from the user input 202 by modifying the size, shape, position, or other aspects of the marker. Such modifications to the marker are provided as a visual feedback mechanism for a user. In addition to the marker modification, the controller may operate on data, or provide an indication to another controller that the data should be operated upon, in a predetermined manner corresponding to the manipulation of the marker. For example, a time interval may be marked off by the manipulation of one or more markers, and the engine 204 may respond, not only by positioning the markers according to user input, but also by computing the time and/or other values (e.g., average signal level over the interval). Additionally, modifications to the position of the marker may be reflected by modifications to information displayed, with, for example, the coordinates of one or more markers displayed and updated "on the fly" as a marker is repositioned on the display. The coordinates may represent a multi-dimensional space in which dimensions are devoted to signal level, time, event number, or other variables, for example. Markers may be combined with other interactive display devices and techniques such as pull-down or popup menus, buttons, or sliders, for example.

In an illustrative embodiment, the interactive display presents electrocardiogram data in a manner that emulates conventional strip-chart recorders. That is, the ECG data are displayed as waveform traces overlaid on a millimeter grid background. In a display mode that may be used as a default, each grid division, or cell, represents 40 milliseconds along the abscissa and 0.1 millivolt along the ordinate. Multi-grid divisions may be "set off" by employing heavier grid lines every fifth division, for example, to form 200 millisecond by 0.5 millivolt "super-cells." A 1280×1024 pixel display that employs an 1220×690 pixel area for the display of waveforms may employ one pixel for every eight milliseconds (five pixels per millimeter) in displaying a standard 1 mm×1 mm, 40 ms×0.1 mV grid. Various "zoom" schemes may be employed to increase or decrease the resolution of the display by increasing or decreasing the number of pixels dedicated to each millisecond and/or millivolt. A user may select one or more features of interest by manipulating one or more markers. Each marker may be a conventional marker, such as a cursor such as is used in word-processing applications, for example. Alternately, a marker may be a vertical line that intersects the waveform and has an associated alphanumeric character, such as a "P" (corresponding to the beginning of atrial depolarization) to identify the meaning of the marked point. The marker may also be iconic, such as a graphic corresponding to a frontal plane QRS axis, for example. Intervals, such as PR, QRS, QT, and RR intervals, may be measured on-screen using one or more markers. That is, for example, a user may employ a single marker to indicate a point for which measurements, such as voltage and time, are desired. The user may use a single marker to set the beginning of an interval for which measurements are desired, then place another marker at the end of the desired interval, or a plurality of markers may be employed to denote data values or data intervals of interest.

Multiple markers may also be employed, with one assigned to mark the beginning of an interval and one assigned to mark the end of an interval of interest, for example. The interactive display system also provides for "automatic" marking. For example, in one mode of operation a user may mark a "Q" feature on a trace of interest in response to which the system completes the markings for the P, J, and T points, or features, and computes the QRS interval and other measurements associated with the marked points and associated medically significant artifact. Measurements may be displayed in close proximity to the measurement marks, overlaid on the strip chart background, and/or may be displayed in one or more separate "reporting areas" on the display. The displayed measurements may be updated continuously, so that, as a marker is moved across the strip chart background, the measurement display continuously changes to reflect the updated position of the marker. Alternatively, the displayed measurements may be updated upon finalization of a marker position. The finalization may be effected through use of an "enter" keystroke, for example.

The time-series data may be obtained directly from an electrocardiogram machine that provides digital output. If the electrocardiogram machine provides only analog output, the analog signal(s) may be converted to digital form for processing by an interactive display in accordance with the principles of the present invention. Whether the analog ECG signals are converted to digital form by the ECG machine or in post-processing, a user may process the corresponding digital data on the interactive display directly from the ECG machine or from stored ECG data.

Figure 3:
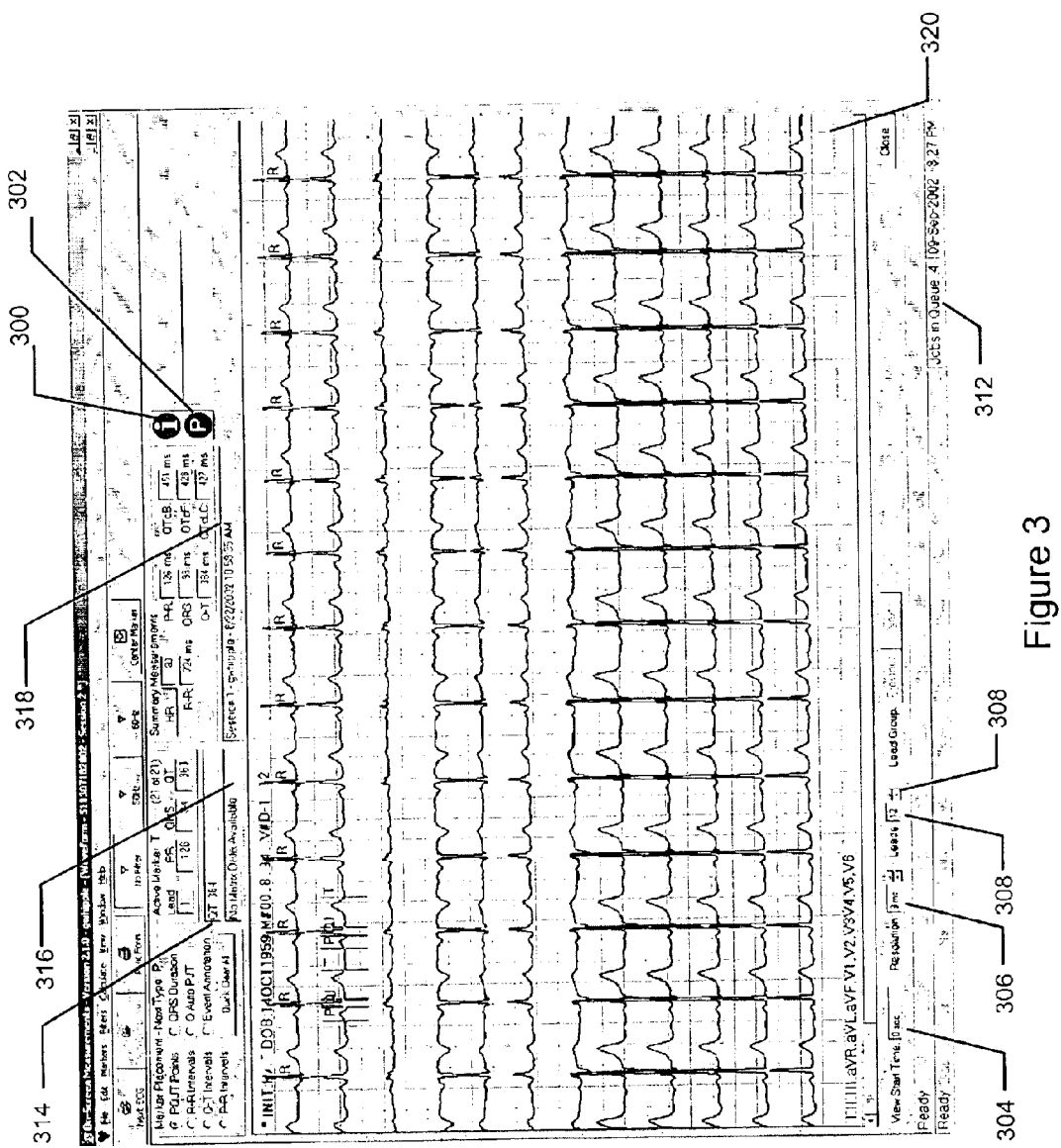
FIG. 3 is an illustrative display screen that contains a standard 12 lead resting ECG in a standard configuration of 10 seconds by 12 leads. This screen is also used to illustrate some of the interactive features and display areas of a display in accordance with the principles of the present invention.

The screen shot of FIG. 3 is illustrative of a display output in accordance with the principles of the present invention. A user may select one or more features of interest by manipulating one or more markers. Each marker may be a conventional marker, such as a cursor such as is used in word-processing applications, for example. Alternately, a marker may be a vertical line that intersects the waveform and has an associated alphanumeric character, such as a "P" (corresponding to the beginning of atrial depolarization) to identify the meaning of the marked point. The marker may also be iconic, such as a graphic corresponding to a frontal plane QRS axis, for example. Intervals, such as PR, QRS, QT, and RR intervals, may be measured on-screen using one or more markers. That is, for example, a user may employ a single marker to indicate a point for which measurements, such as voltage and time, are desired. The user may use a single marker to set the beginning of an interval for which measurements are desired, then place another marker at the end of the desired interval, or a plurality of markers may be employed to denote data values or data intervals of interest.

Multiple markers may also be employed, with one assigned to mark the beginning of an interval and one assigned to mark the end of an interval of interest, for example. The interactive display system also provides for "automatic" marking. For example, in one mode of operation a user may mark a "Q" feature on a trace of interest in response to which the system completes the markings for the P, J, and T markers and computes the measurements associated with the beat, that is, the PR interval, the QRS duration, and the QT interval. Once a typical set of markers have been placed, the system may sequence through all beats and place markers for these points. The system may operate through other automatic sequences related to the selection of particular measurement points, such as the location and measurement of a point to measure ST elevation or depression. An operator may define a set of marks as an auto-sequence to allow the system to replicate measurements based on the sample markers placed during the definition. Sequences of marks may be automatically placed either through operator initiation of the operation or based on specific requirements for sets of ECGs where annotation marks will be automatically placed for operator verification. Such features as automatically marking the peaks of waveform features as well as the onset and offset of detailed features are supported by the principles of the present invention.

Measurements may be displayed in close proximity to the measurement marks, overlaid on the strip chart background, and/or may be displayed in one or more separate "reporting"_ areas on the display. For example, in the illustrative screen shot of FIG. 3, an information button 300 may be used to alert an operator in some way. For example, in this illustrative screen shot, the button 300 features a white button on a red background to indicate an emergency read condition. By activating the button (e.g., by "clicking on" the button) the operator may obtain more information related to the ECG data set, related, for example, to the nature of the emergency. Various indicators, such as flashing, color changes, the use of specific colors, different levels of transparency, and other display techniques may be used to alert an operator to various conditions related to the button 300 or other features displayed on an interactive display in accordance with the principles of the present invention. Other conditions may be signaled by operation of the button 300. For example, a blue background with a white "i" substituted for the X, may be used to indicate that further information is available to an operator and that it may be obtained by clicking on the button 300. Protocol information may be obtained through activation of the protocol button 302. In this illustrative example, the start time, resolution of the display, and the number of leads for which data are displayed are respectively displayed in windows 304, 306, and 308. The windows may include up/down arrows, such as arrows 310 to allow an operator to select different resolutions or number of leads displayed, for example.

The display may also include an indication of the number of jobs waiting to be serviced, as indicated by the window 312. The start time is the initial offset of the starting point on the screen with reference to the beginning point of data collection. The "resolution" feature included in this illustrative display indicates the relationship of the waveform display to the physical display. The 8 ms resolution means 8 ms/pixel. This is the standard starting display resolution in this illustrative embodiment. By decreasing the resolution, the magnification of the displayed waveform is increased. Decreasing the resolution to 4 ms would double the size of the displayed wavefonn The display of the background millimeter grid is also based on the resolution setting. If the number of pixels on the display between 1 millimeter grid marks would cause the grid to make the waveform difficult to read, the background grid is reduced to 5 millimeter increments. An option is also provided to temporarily eliminate the background grid if desired. The invention is not limited to the concept of using the smallest viewable feature of the display as the maximum resolution. The "Leads" option 308 permits an operator to increase or decrease the number of leads that are displayed vertically on the screen. The system will attempt to optimize the number of leads being displayed based on average waveforms or on the amplitude of the waveforms being presented. This option allows viewing a single lead regardless of the magnification. The "Jobs in Queue" field 312 indicates to an operator the number of separate "tracings", e.g., ECGs, waiting to be processed by the operator on the system. In an illustrative embodiment that employs a display that utilizes 1220 ×690 pixels of display area for the display of traces, when 8-millisecond resolution is selected, the screen is able to display 10 seconds of data. At 4-millisecond resolution, 5 seconds of data can be displayed. The resolution indicates the amount of time represented by each screen pixel as well as the change in marker location when the left or right arrow keys are pressed.

Summary measurements may be displayed in windows labeled HR, Max P-R, Max QRS, Avg R-R, Max Q-T, and QTc, for example. The type and sequence of marker(s) to be placed on a display may be selected from the Marker Placement display menu. The options in this menu include areas labeled PQJT Points, R-R intervals, Q-T Intervals, P Intervals, QRS Duration, Q auto PJT, and Event Annotation, for example. Data associated with lead containing the "active marker", that is, the marker currently being manipulated, may be displayed in the windows labeled Lead, PR, QRS, and QT. Additional windows, such as windows 314, 316 and 318 may be used to display such information as the values for all measurements based on the current active marker (indicated in box 314), and the specified calculated values for all measurements in the currently active lead. Items 316 and 318 are display boxes that provide information about data that has been provided with the current ECG. This information includes previously calculated measurement values that have been provided and when the last review of the ECG was done and by whom.

In an illustrative embodiment, the waveform display area includes 5-mm grid lines 320 for reference. Each grid division represents 200 ms in the time dimension and 0.5 mV in the voltage dimension. The perspective of the waveform may be maintained during a "zoom" operation by magnifying the horizontal and vertical dimensions of the waveform by the same amount. In an illustrative embodiment, the interactive display supports zoom operations that allow an operator to place markers with greater precision than a full-screen twelve-lead display might otherwise permit. The number of pixels between grid lines varies in the process of zooming and 1 millimeter grid lines may be added during a "zoom in" in order to provide the standard recognizable grid background for visual reference. Conversely, 1 millimeter grid lines may be deleted during a "zoom out" operation in order to avoid cluttering the display. Five millimeter grid lines will always be present (unless the grid line display option is turned off). In an illustrative embodiment, a five-pixel threshold is employed whereby 1 mm grid lines are added to the display when five or more pixels are required to display a distance equal to one mm. To provide additional context, every fifth grid line may be distinguished from the other grid lines by displaying them wider, darker, or in a different color, for example.

The display may provide for a variety of display modes, depending on the available data and the preferences on the operator. For example, a complete 12 lead resting ECG may be displayed as 12 leads by 10 seconds. It may also be displayed as 2 five second groups of 6 leads each. Depending upon the display output device, display magnification, also referred to herein as zooming, may cause a portion of the data to exceed the display area available at any one time. The display may provide horizontal and/or vertical scrolling to provide access to such display information. Additionally, as the magnification of a waveform is increased, the number of leads that can be displayed vertically without overlap may be reduced. The number of leads to be displayed can either be set automatically by the program to optimize the number of lead to be displayed or it can be manually selected to increase or decrease the number of leads being displayed. An operator may select a subset of the 12 leads to be displayed.

The waveform's trace should be wide enough and heavy enough to make it readily viewable at a nominal viewing distance, yet should not be so wide and heavy as to obscure the waveform features. In an illustrative embodiment the waveform is plotted on the screen with the minimal line width that makes the waveform readily viewable with the reference grid. However, the display includes a facility that allows an operator to adjust the waveform trace's line-width to conform to the operator's visual requirements.

Figure 4:
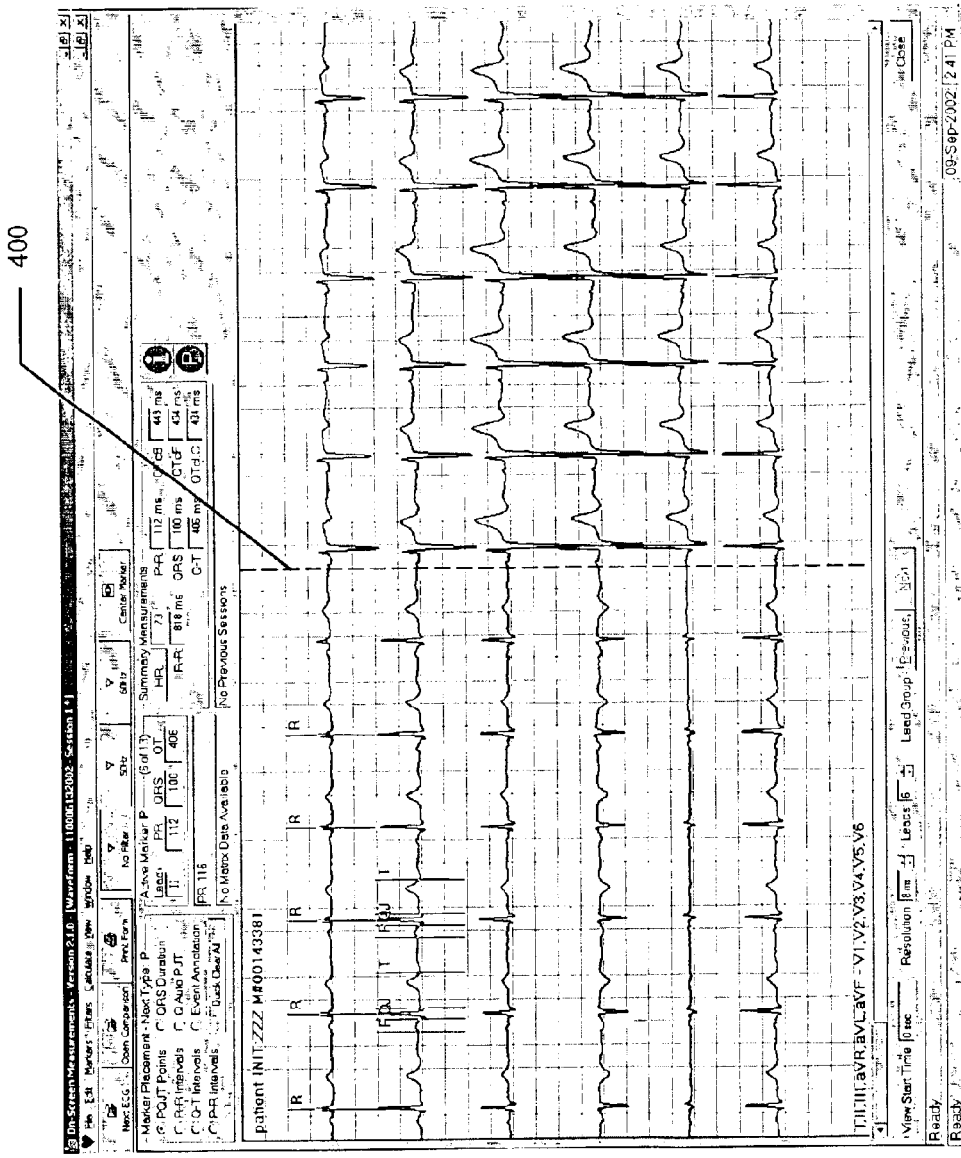
FIG. 4 is an illustrative display screen that contains another format of a standard 12 lead resting ECG—2 groups of 6 leads with 5 seconds of data per lead group. This screen is also used to illustrate some of the interactive features and display areas in accordance with the principles of the present invention.

The screen shot of FIG. 4 illustrates an alternate 12 lead waveform display screen view in accordance with the principles of the present invention. A vertical line 400 separates the display into two sets of six leads each. In this illustrative embodiment, the I, II, III, aVR, aVL,and aVF lead data are displayed on the left-hand side of the vertical line 400 and the V1, V2, V3, V4, V5, and V6 data are displayed on the right-hand side of the vertical line 400. The right- and left-hand sides of the display may be sequential depending on the available data. That is, for example the data plotted for the V1 lead starts at the time the data plotted for the I lead ends. This display format may also be used to display waveforms that are not acquired simultaneously. A number of markers have been placed on the screen. In this illustrative embodiment, the markers are vertical lines used to designate the exact position chosen by an operator. Additionally, the markers are multi-part, in that they are accompanied by alphanumeric labels (e.g., P,Q J, etc.), corresponding to familiar labels given to ECG features.

Figure 5:
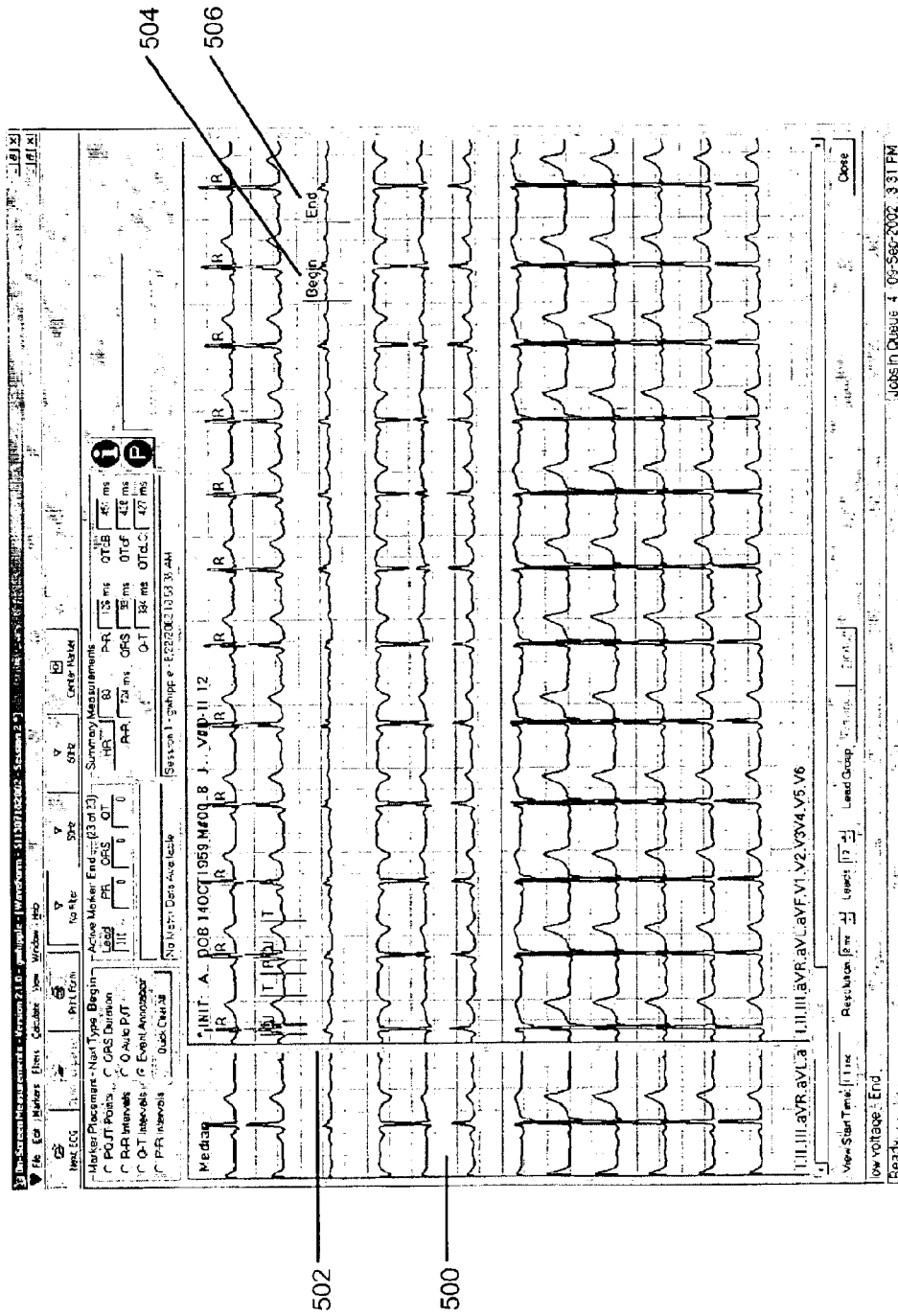
FIG. 5 is similar to FIG. 3 with the addition of the display feature to include the presentation of a median beat or other derived data. This figure also illustrates the placement of annotation markers to identify waveform features in accordance with the principles of the present invention.

The screen shot of FIG. 5 illustrates a split-screen display in accordance with the principles of the present invention in which a "pane" 500, delineated by vertical line 502, may be opened to display median heart beats or other derived waveform data. The median beats pane is automatically sized to display the entire beat, and so does not scroll with the rhythm waveforms. In an illustrative embodiment an interactive display in accordance with the principles of the present invention provides one or more markers, such as markers 504 and 506, for use by an operator in an on-screen measurement process involving one or more displayed time-series waveforms. Markers 504 and 506 include alphanumerical components, indicating, in this instance, the beginning and end of an interval measurement. The markers are used to identify on-screen measurement points and are plotted vertically and identified with a label of the point or event that is being identified: the "begin" and "end" labels in this example. In an illustrative embodiment, when a marker is associated with a single lead, the marker will be limited to the plot area occupied by that lead. When global measurement marks are being used, the mark will extend from the top to the bottom of the plot screen area. The width of the markers may be selectable as an option. Initial placement of the markers may be with the use of a light pen or mouse pointer and a click. Once a marker has been placed, it becomes the "active" marker. The active marker can be moved left or right, with the resolution of one pixel at a time. When moving a marker, the time increment (the time represented by each pixel) will vary depending on the selected resolution. The active marker is the one most recently added, or one that has been selected. The active marker may be selected using a keyboard, mouse pointer, or light pen, for example. The interactive display may provide visual feedback to a user by, displaying the active marker with a different color than other displayed markers, by flashing the marker, or using other display techniques. An interactive display in accordance with the principles of the present invention may also allow a user to select the color of markers and to select the means of highlighting the active marker.

As previously noted, in accordance with the principles of the present invention, a twelve-lead resting ECG may be displayed in the format normally presented on the printed page. Lead I and lead V1 will be plotted on the same line with lead V1 starting at exactly 5 seconds after the start of lead I. The other sets of leads will be plotted in the same manner: II and V2, III and V3, aVR and V4, aVL and V5, and aVF and V6. The waveforms for the 60 seconds of rhythm data will be displayed as a single lead continuous string of waveform data. This format supports making sequences of measurements across the entire set of data. The single or multi-lead waveforms for 60, 120 seconds, or longer sets of rhythm data may be displayed, for example.

Figure 6:
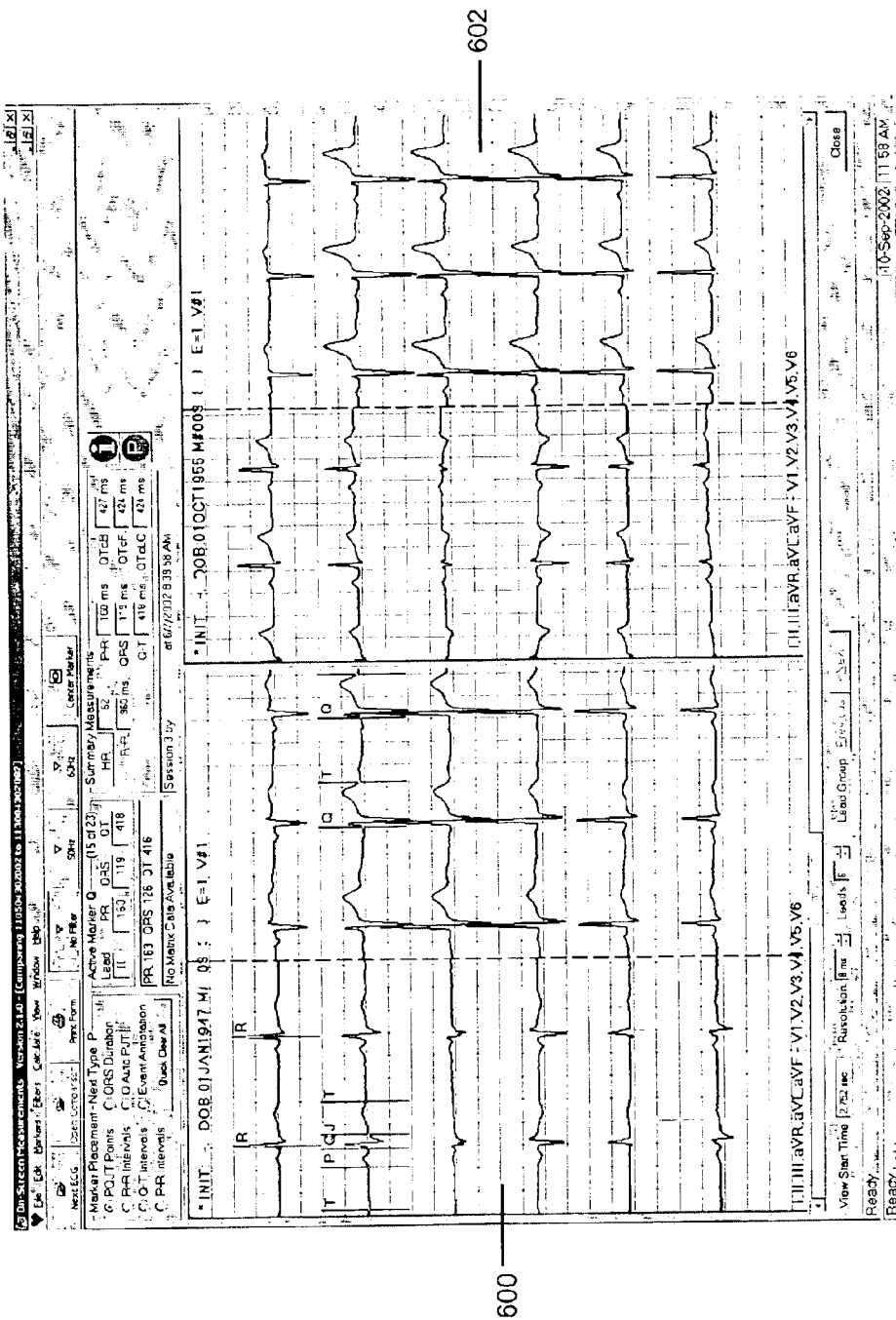
FIG. 6 is similar to FIG. 4 with the addition of the display feature to include the presentation of a comparison ECG waveform in accordance with the principles of the present invention.

As illustrated by the screen shot of FIG. 6, comparison ECGs may also be displayed, using toolbar activation, file menu selection, or other user interface techniques. In an illustrative embodiment, the interactive display permits an operator to view a comparison ECG on its own, or, as illustrated, in a side-by-side configuration of two panes 600 and 602. Report text associated with the comparison ECG may also be displayed under operator control, by selection from a popup menu, for example. A plurality of comparison ECGs may be viewed, for example by selecting "next comparison" from a popup menu.

Figure 7:
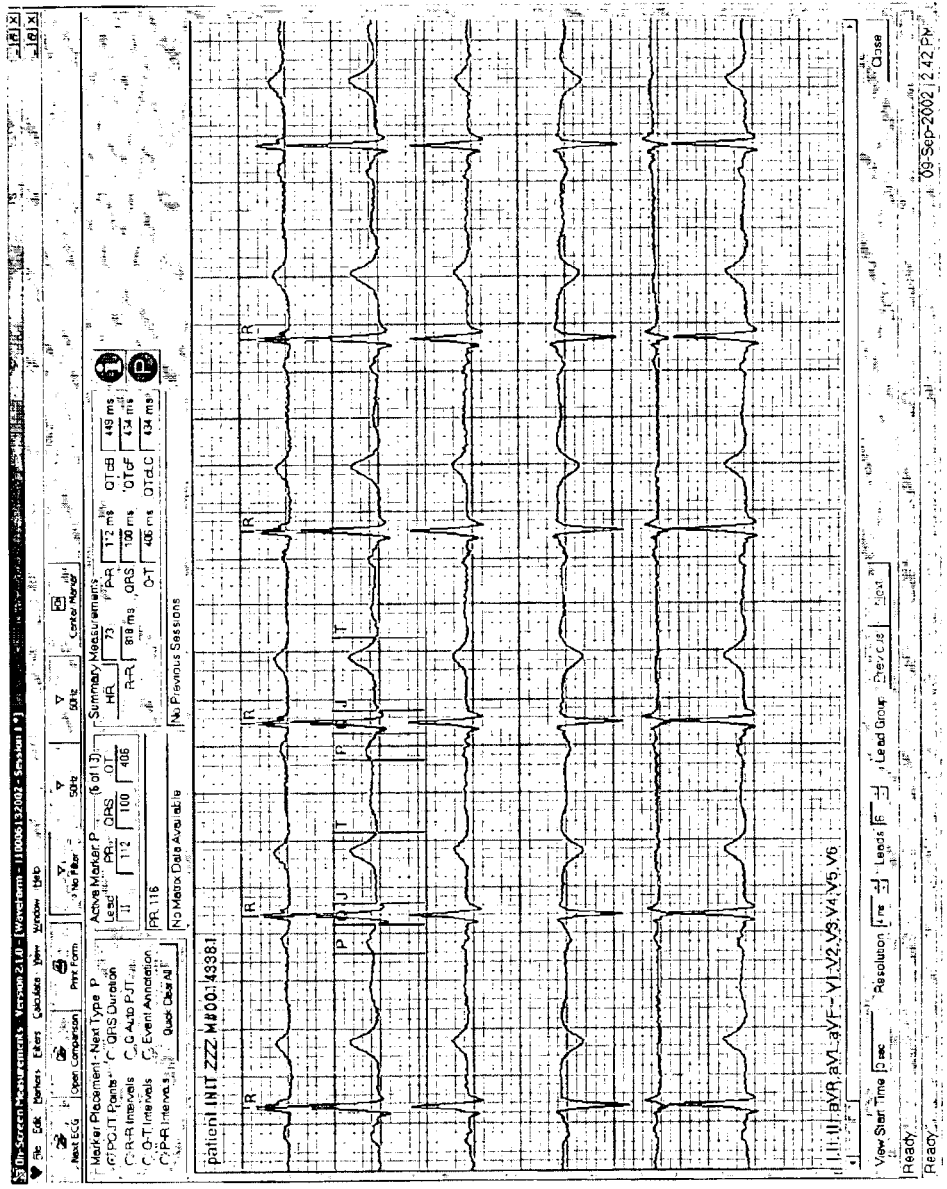
FIG. 7 is an illustrative display screen that shows a 2× expanded waveform to illustrate the equal expansion of the vertical and horizontal aspects of the waveform display in accordance with the principles of the present invention.

The screen shot of FIG. 7 will be used to illustrate in more detail the placement of markers on an ECG display in accordance with the principles of the present invention. To place a marker on the waveform, the user may select a marker placement sequence by clicking on a marker placement control: one of the chad-like selection mechanisms labeled PQJT Points, R-R Intervals, etc. The interactive display will start with the first mark in the selected sequence and will provide subsequent markers in the proper sequence. An interactive display in accordance with the present invention also permits an operator to annotate events, for example, by marking the beginning and end of a section of a Lead wave and attaching descriptive text to that segment. Such markers may be used to delimit and describe a section of the Lead wave without creating a measured interval. In particular, they may be used to delimit and describe a section of the Lead wave, such as an ST depression, or abnormal U-wave. In an illustrative embodiment, when one of these markers is selected, its descriptive text is displayed in the Status Bar at the bottom of the form. In an illustrative embodiment, a sequence of markers may be placed by an operator clicking and hold the left mouse button to initiate marker placement. The interactive display may then display a dotted vertical line to indicate where the marker will be placed. The user may then move the mouse to the desired location and release the button to place the marker. The selected marker placement sequence (Q Auto PJT in this example, would first place the Q marker), will determine the next marker type to be placed. The label for the next marker is displayed in the marker placement control.

In an illustrative embodiment, after placement, the active marker position can be adjusted using arrow keys or other user input devices. To select the active marker using an arrow key implementation, the user may press shift and the left or right arrow key until the desired marker is highlighted, for example. To move the active marker, the user could then press the left or right arrow keys or use an alternate graphic input device to indicate the marker should be moved. In this illustrative embodiment, each time the arrow key is pressed, the marker moves by the amount indicated in the current resolution and interval calculations are instantly updated as a marker is moved. An interactive display in accordance with the principles of the present invention may also provide keystroke functions to select the first and last markers as the active marker and to shift the area of the waveform being displayed. The Home key or some other indicator may be used to center the active marker in the viewable screen area.

Figure 8:
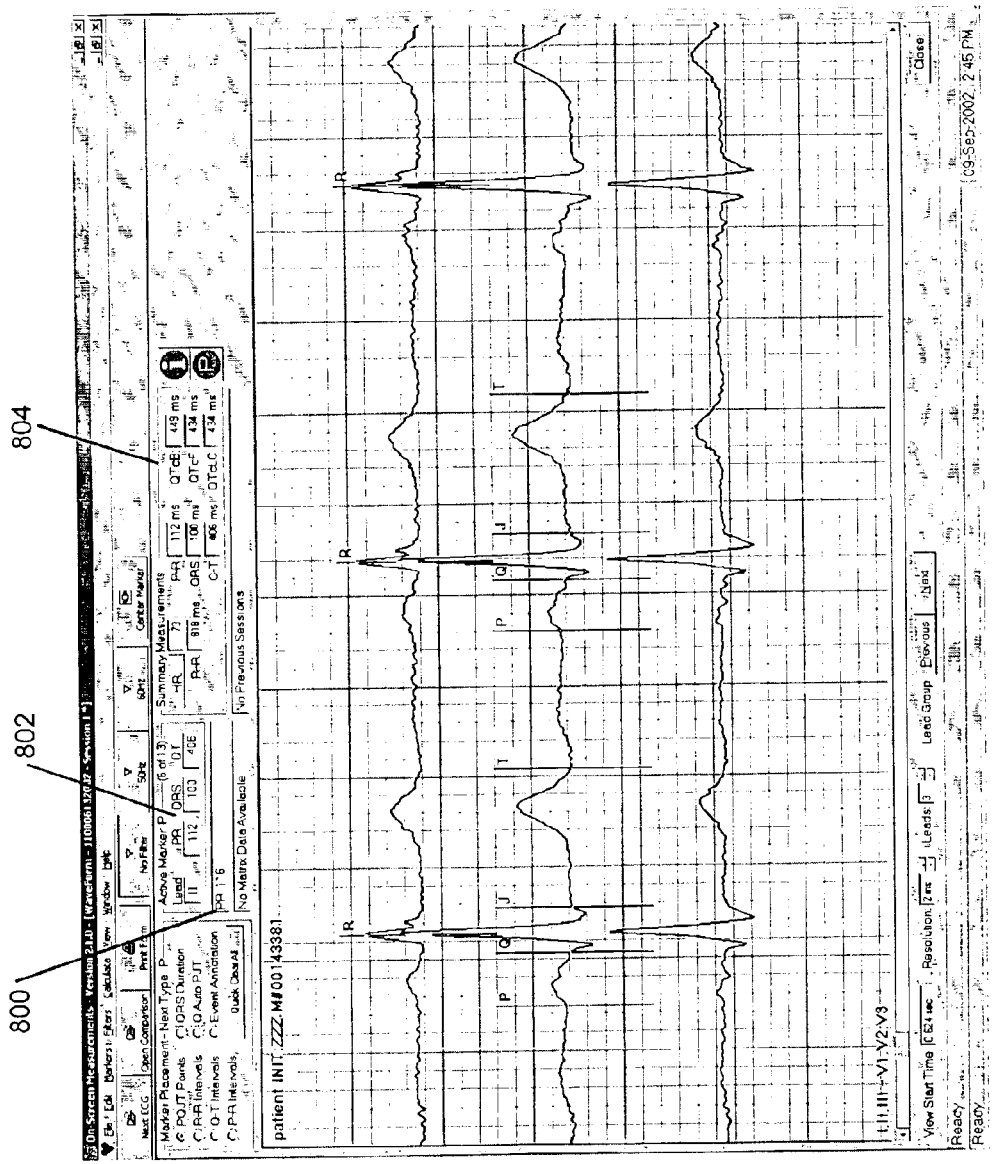
FIG. 8 is an illustrative display screen that shows examples of the waveform measurement display for the current marker, the current lead, and the overall summary measurements in accordance with the principles of the present invention. This figure also shows a 4× expanded waveform display in accordance with the principles of the present invention.

The screen shot of FIG. 8 illustrates the display of active marker data in accordance with the principles of the present invention. When matching sets of markers have been placed, intervals are calculated from their positions and displayed in several boxes at the top of the waveform. In the active marker area 802, the intervals calculated using a method for the current lead (the lead containing the active marker) are displayed. The method used for calculation of the measured values may be selected by the operator or may be set by information which accompanies the ECG waveform data. Directly below that (800) are displayed all intervals with which the active marker is associated; moving the active marker will typically impact both of these sets of intervals. In the summary measurements area 804, the overall measurements are displayed; these measurements are derived from markers on all leads. The calculated values may represent, for example, either the maximum lead average for which multiple intervals are marked, or the overall maximum of each measurement, depending on the current setting of the summary measurement calculation option. Placing the mouse pointer over the Max P-R, Max QRS, or Max Q-T values will present a ToolTip displaying the Lead on which the maximum value was found. In addition, double-clicking on the Max P-R, Max QRS, or Max Q-T values will highlight and make active the Markers representing the maximum measured interval of that measurement.

Figure 9A:
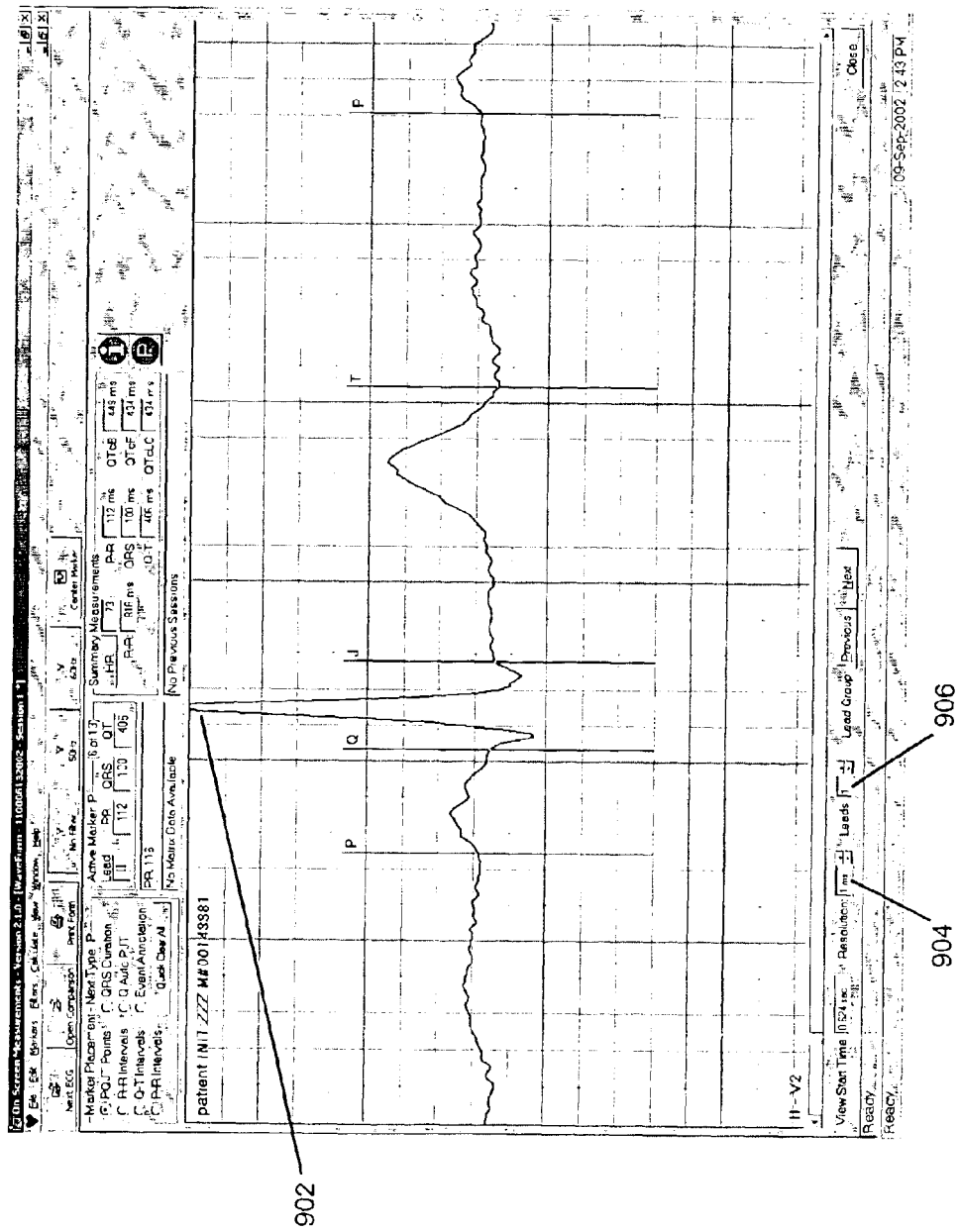
FIG. 9A is an illustrative display screen that shows a 8× expanded waveform to illustrate the equal expansion of the vertical and horizontal aspects of the waveform display in accordance with the principles of the present invention. This figure also illustrates the ability to display a single lead for detailed analysis in accordance with the principles of the present invention.
Figure 9B:
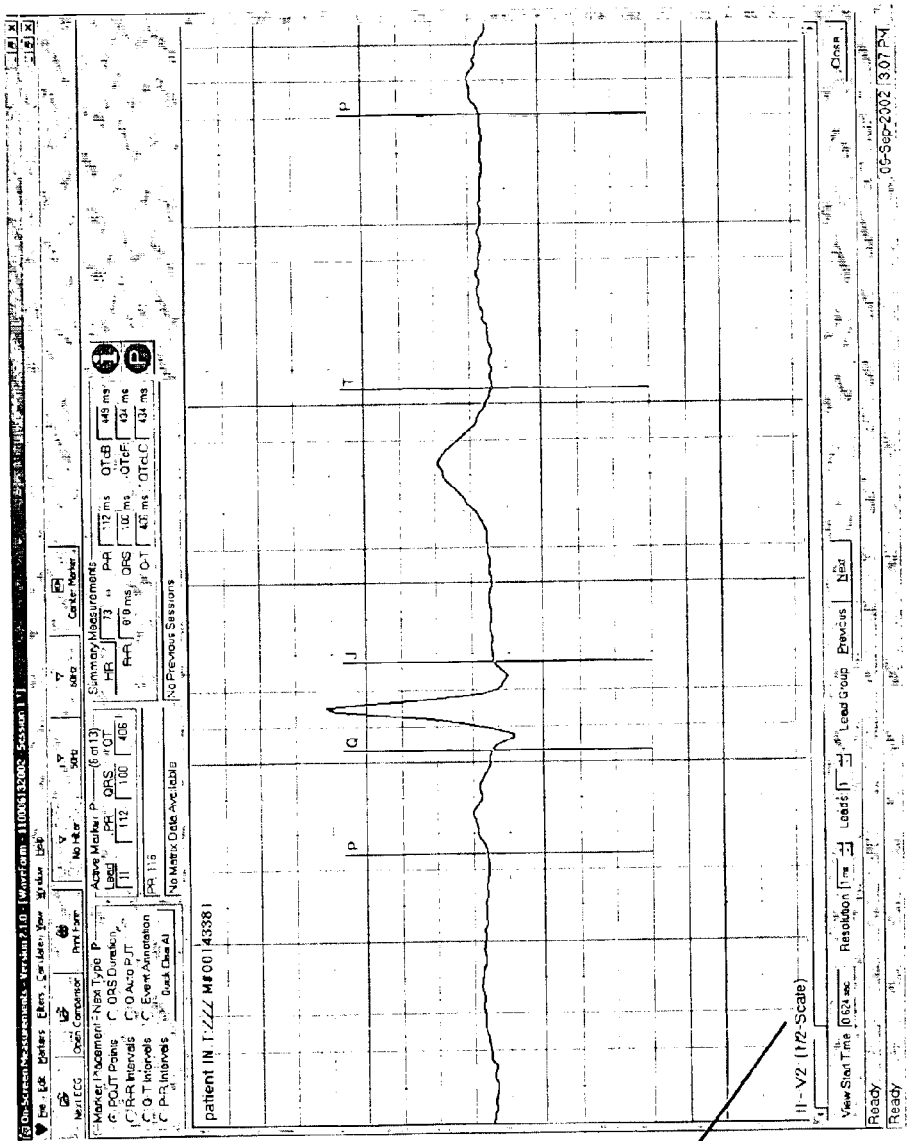
FIG. 9B is an illustrative display screen that shows an example of the waveform in FIG. 9A displayed at ½ scale (vertical scale is reduced to ½ while the horizontal scale is maintained) in accordance with the principles of the present invention.

The screen shots of FIG. 9A and FIG. 9B illustrate the use of a half-scale display in accordance with the principles of the present invention. This optional view may be used, for example, for an ECG that exhibits very high amplitudes, resulting in the waveforms being drawn outside the top (902) or bottom of the display area or overlapping each other. Note that the scale option may be exercised independently of the resolution option. When the half-scale display option is selected, this status is indicated with an on-screen display 910 and with changing the color or other attribute of the plotted waveform, for example. Various filter options are accessible, in this illustrative embodiment through interaction with a toolbar. For example, as indicated by the tool boxes labeled "No Filter", "50 Hz", and "60 Hz", a operator may select 50 Hz, 60 Hz, or no filtering of the ECG data. These filter options may be used to assist in the analysis of noisy data without affecting the original data, for example.

Figure 10:
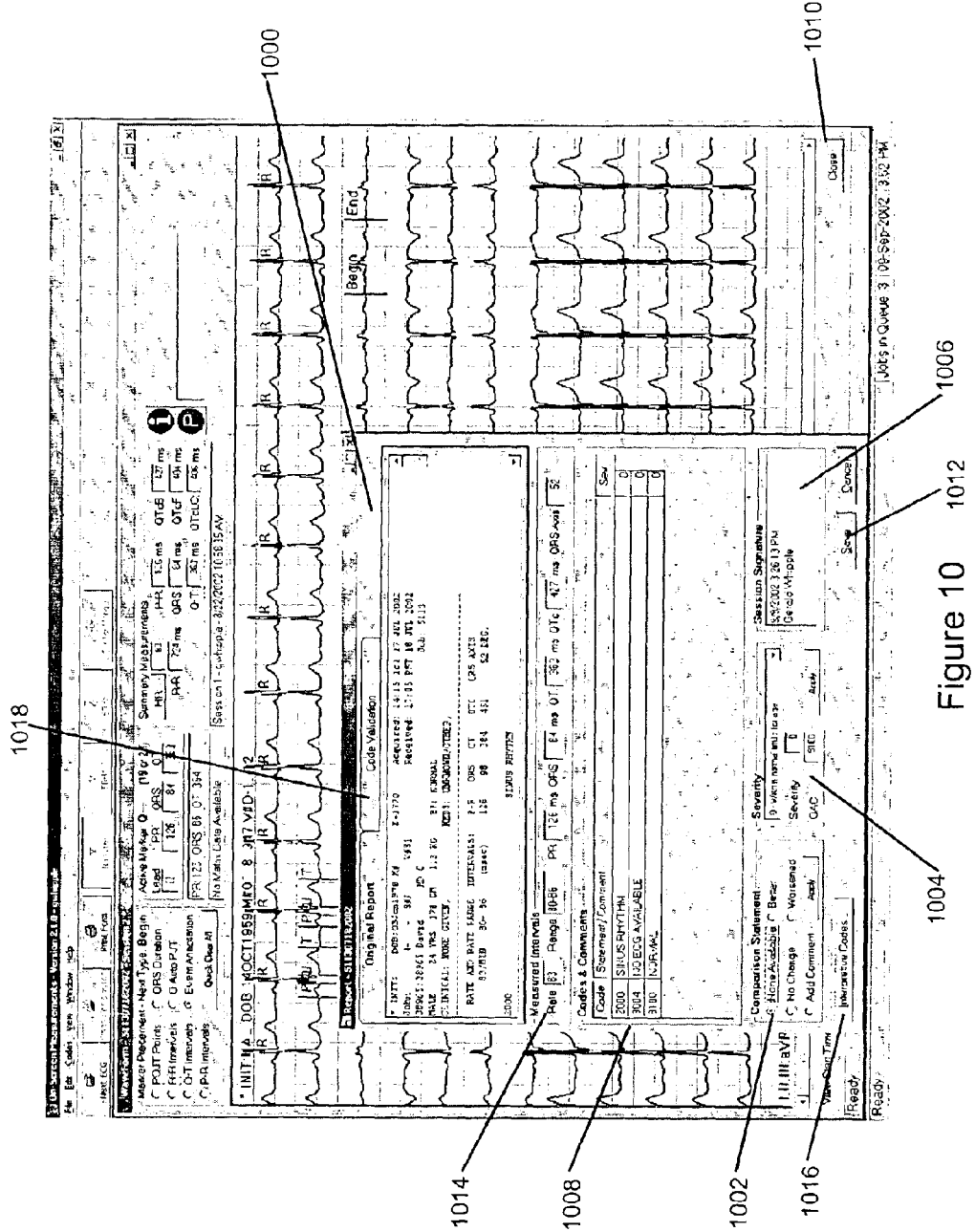
FIG. 10 is an illustrative display screen that shows an example text report display and editing function with related data entry and option selection features in accordance with the principles of the present invention.

The screen shot of FIG. 10 depicts a report form format for an interactive display in accordance with the principles of the present invention. The report form includes a window 1000 that displays report information. The Original Report Text area can be used to display the results of a computer analysis of the ECG or the results of a previous operator review, for example. The Measurement Intervals area 1014 can display the results of the calculations used to determine measurement values from the markers and that will be included in the completed report. The Codes and Comments area, field 1008, may be used to enter interpretive and diagnostic codes and statements and additional comments that are to be part of the completed report. The values in this area may be preset by computer interpretation, prior review, or other data that may accompany the ECG, such as the customer ID number, for example.

In this illustrative embodiment, the interactive display includes a field 1002 of comparison statements selection options that may be used to conveniently note trends in ECG data for a particular patient based on a previous ECG. An operator may also employ the severity field 1004 to enter information related to the overall assessment of the ECG. A session signature field 1006 may be used to display the current date and time and the identification of the current operator. A separate entry is required by the operator to be the electronic signature for the set of entries.

In this illustrative embodiment, the display includes a Save function 1012 to indicate that the report editing process is complete.

In this illustrative embodiment, the display includes an Interpretive Codes function 1016 to allow the selection of interpretive codes from a menu. An illustrative embodiment of the code menu selection screen is shown in FIG. 11.

Figure 11:
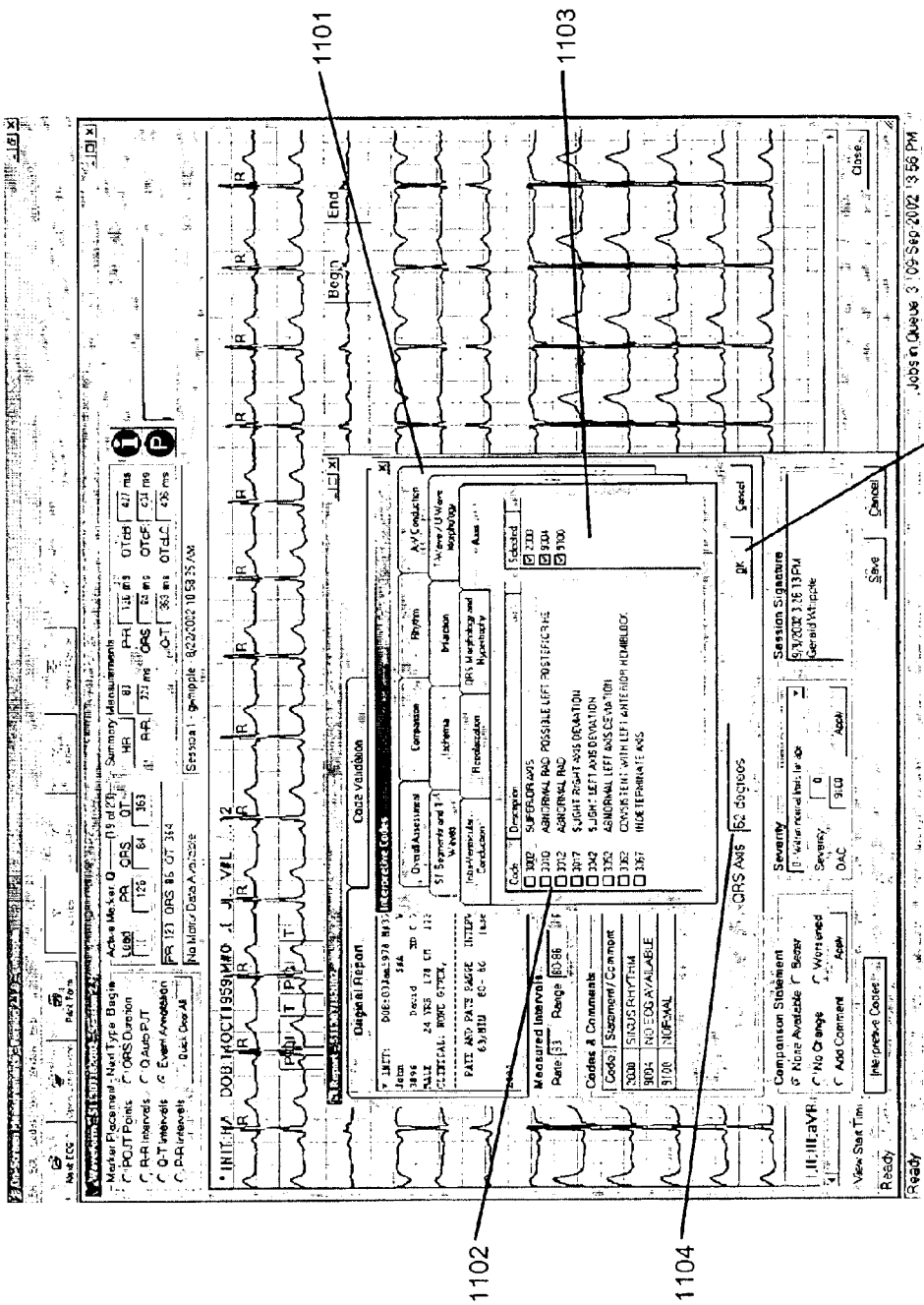
FIG. 11 is an illustrative display screen that shows an example that extends the editing features to include the menu selection of coded and textual statements that will become part of the ECG report in accordance with the principles of the present invention.

As illustrated by the screen shot of FIG. 11, an interactive display in accordance with the principles of the present invention provides a tool for an operator to select among a variety of interpretive codes. The types of codes are indicated by folder tabs 1101, marked "overall assessment", "comparison", "rhythm", A-V "conduction", "ST segment", etc. Each tab contains a set of code numbers and text related to the label on the tab. These code values, when selected, will be placed in the codes and comments section, field 1008, for inclusion in the report. The complete list of selected codes is displayed for reference in window 1003. Provision is made for changes to measurements or observations that are not determined by markers, the QRS axis for example 1104. Placing the selected codes in the Codes and Comments are 1008 is accomplished by clicking on the OK button 1105, for example.

Figure 12:
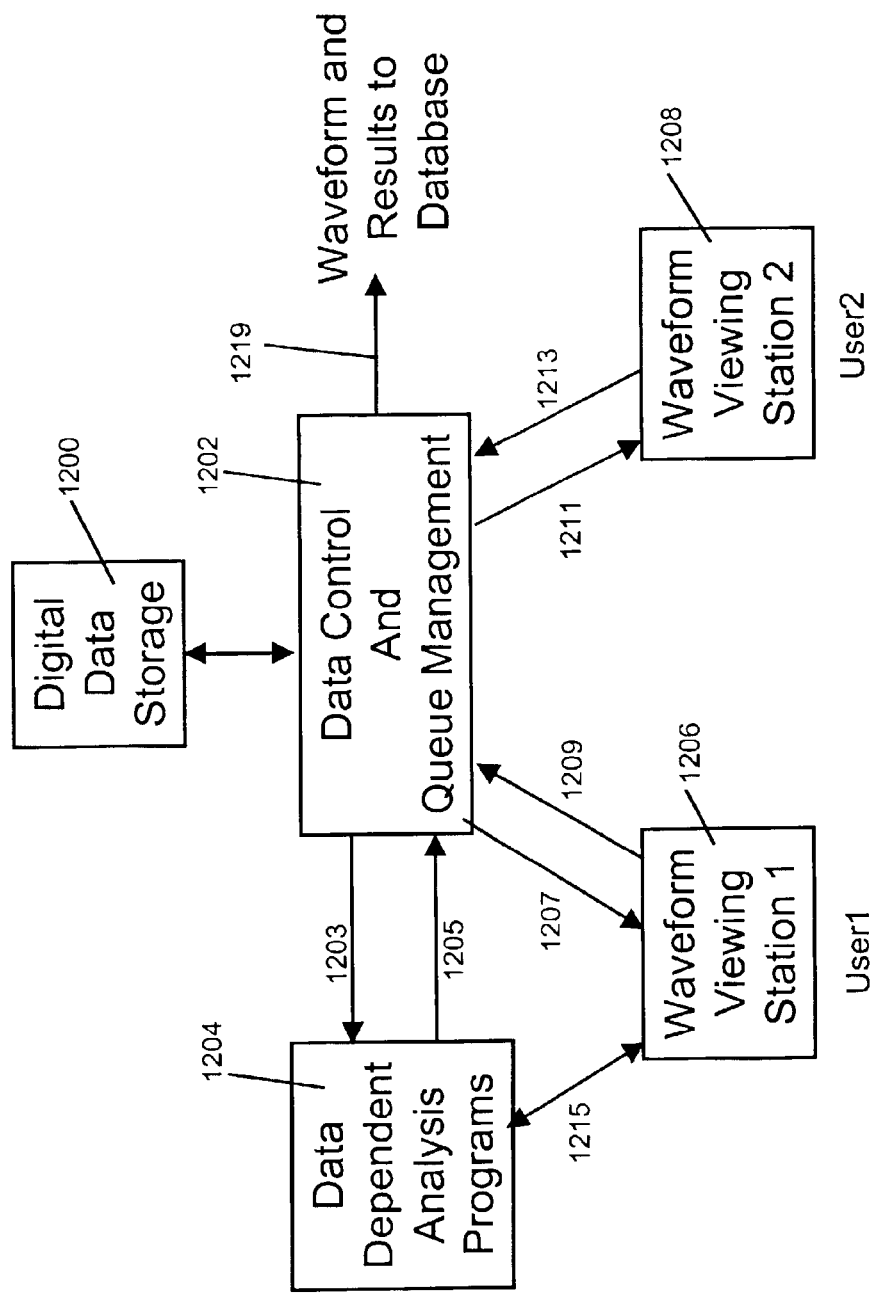
FIG. 12 is a conceptual block diagram of a system that may employ more than one interactive display in accordance with the principles of the invention. This diagram shows the potential interactions between system elements and interactive displays in accordance with the principles of the present invention.

Additionally, one or more users may use an interactive display in accordance with the principles of the present invention to process ECG data that is obtained at one or more patient sites and transmitted, via a telecommunications network, for example, to an ECG analysis center. The block flow diagram of FIG. 12 depicts the flow of processing ECG data in a central processing center in accordance with the principles of the present invention. Processes illustrated through the use of flow charts or block flow diagrams may not be strictly linear processes and alternative flows may be implemented within the scope of the invention. The specific configuration of logic and/or instructions utilized to achieve a particular function, as well as other modifications to the inventive concept are contemplated within the scope of this invention.

In a time-series data processing center in accordance with the principles of the present invention, digitized ECG data 1200 may be transmitted to an analysis center and stored for future processing or placed in a queue for immediate processing. Alarms of varying degrees of urgency may be activated by an interactive display in accordance with the principles of the present invention in response to ECG data analyses. In addition to ECG data, the data 1200 may include the serial number of a unit, such as an ECG machine, revision code of program, data control card number, type of test being transmitted (12 lead, 60 second, 120 second rhythm and related lead), whether this particular ECG set has been transmitted before, whether battery voltage is low, for example.

In this illustrative embodiment, data is received and temporarily stored in a data control and queue manager 1202. After the file is received by the data control and queue manager (which could be an instantiation of an object class, for example) 1202 the data file is sent in step 1203 to data dependent analysis programs 1204. The computer analysis program determines annotation points and creates tables of measurements from these points. The analysis program may also infer, from these measurements and other data provided with the ECG, an assessment and interpretation of the ECG.

The results of the analysis may be recorded in a report format similar to the intended output of the invention. Different analysis programs may be necessary to perform different sets of measurements and interpretations based on the type of ECG data being provided and the reason for processing the ECG. Some or all of the results of the computer analysis may be made available to the system incorporating the invention to provide initial marker points or additional information about the ECG waveform.

In step 1205 results from these programs are shipped back to the data control and queue manager 1202. From there, the results (which include measurements and waveform information) are sent to a viewing station 1206 in step 1207. At this point, an operator, User 1, may enter or modify markers used to determine interval measurements, for example. If changes are made, the updated data may be returned to the data dependent analysis programs in step 1215 and the files are sent back to the queue manager in step 1209.

The "marked up" waveform data, with markers and intervals, may be sent to a viewing station, 1208, in step 1211. Although the viewing station 1208 may be the same viewing station, in an illustrative embodiment the viewing station is a separate viewing station for use by a second operator, User2. User 2 views the data and adjusts the markers as he feels necessary. User 2 may make, for example, changes and additions that he feels are necessary, along with his comments and observations about the waveform. The end results, including all annotations, are transferred in report and results files in step 1219 to an automatic importer. In an illustrative embodiment, a plurality of viewing stations 1206 may receive time series data, such as ECG data, with the data distributed by the data control and queue manager 1202 using call-center routing. In such an embodiment, incoming calls (e.g., ECG data) may be directed to the next available user. However, calls need not be processed in the order in which they are received at the center. For example, emergency calls may be given the highest priority, with other calls being assigned descending priorities depending on their processing requirements.

As an illustrative example, the process whereby an ECG or other time series data may be reviewed by a sequence of 2 users at two interactive viewing stations in accordance with the principles of the present invention is shown in FIG. 12. The processing sequence may be controlled by 1202 Data Control and Queue Management based on the user capabilities, ECG specific processing requirements, or general processing requirements, for example. As an illustrative example, additional user review steps may be added to the sequence if indicated by processing requirements.

Figure 13:
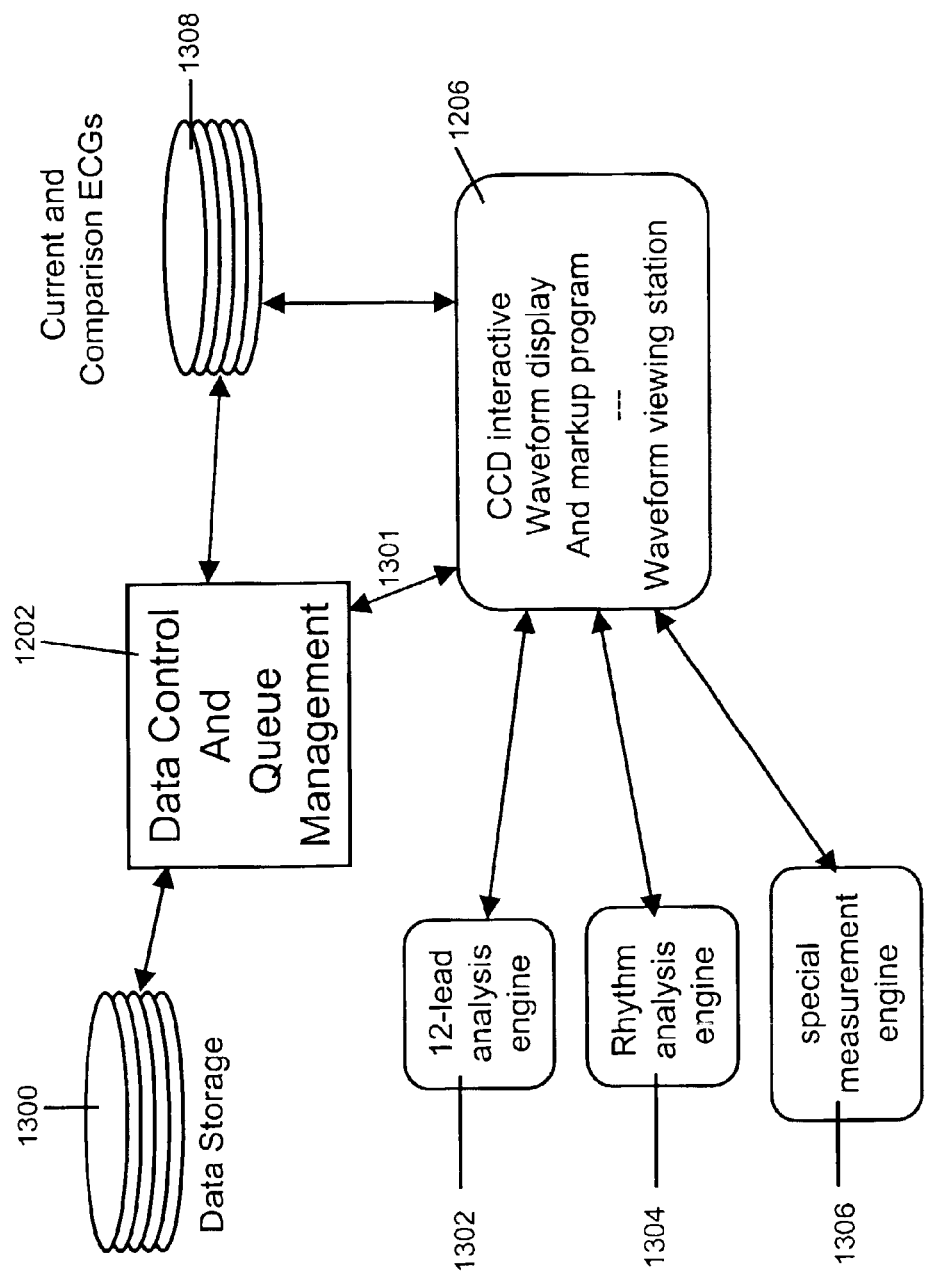
FIG. 13 is a conceptual detailed block diagram of a system that may employ additional analysis functions in support of the interactive display in accordance with the principles of the invention. This diagram also illustrates how the system may employ additional queuing and data control functions in support of the interactive display in accordance with the principles of the invention.

The block flow diagram of FIG. 13 illustrates in greater detail the process whereby a user may review, change and approve a processed ECG file in accordance with the principles of the present invention. Data, report and results are stored in storage 1300 and made available to a technician's workstation 1206 through the data control and queue manager 1202. For the user's review, the queue manager 1202 sends current and comparison ECGs, in the form of report and results files to interactive display 1206 in step 1301. Analysis and measurement programs, which reside in this illustrative embodiment on the interactive display in accordance with the principles of the present invention, include a 12— lead analysis engine 1302 to provide full detailed measurement and analysis of the ECG waveform or to provide a re-assessment of the waveform based on changes made by the operator, a rhythm analysis engine 1304 to provide a test specific set of measurements and assessments for single or multi-lead rhythm tests, and a special measurement engine 1306 to provide non-standard measurements and assessments of 12 lead resting ECGs, rhythm strips or other time series data that may be collected and presented. In accordance with this illustrative embodiment, a user can accept marked measurements, reject marked measurements (by moving one or more markers), reprocess an interpretation if measurement changes are made, or select alternative analysis/measurement processing.

The Current and Comparison Data Storage (shown in 1308) includes ECG job data, patient demographic data, customer specific processing requirements, account information, such as a patient site and sponsor data, complete waveform display data, and the complete report text. The report file and associated measurement and database files retain the original computer measurements and interpretation and the history of all completed reviews and processing, including the latest cardiologist revisions. The results file and associated files and databases contain marker and measurement information entered or calculated by the system to allow annotation points and measurements to be displayed by the invention. This includes: complete measurement matrix values from the analysis program, such as detailed measurement values for features in each lead, for example; sample point locations and values for each of the following items for each of the 12 leads: such as P onset, P amplitude, P duration, Q onset, Q amplitude, Q duration, R onset, R amplitude, R duration, S onset, S amplitude, S duration, J point, J level, J+80 ms level, T onset, T amplitude, and T duration, for example. Multiple sets of sample location points will be stored when special measurements have been made. Each time a change is made to the contents of the results file, all old results are retained and the new results are appended with the appropriate identifiers, including reviewing operator, date, and time. In an illustrative embodiment, each time a session is completed, the system requires the entry of a password to verify the identity of the operator.

As illustrated in FIGS. 10 and 11, the current invention supports the entry of codes, text and comments related to the interpretation of the time series data being presented and marked for measurement. In the current invention, these entries may be checked for validity against each other and against the measurements determined by the markers as part of a Quality Assurance process. The validity checking may result in not allowing certain combinations of contradictory entries or it may allow entries to remain with confirmation that unusual values or combinations of entries are correct. The Code Validation tab 1018 is used to display the results of this analysis for correction or confirmation.

A user may select among various views and magnifications of ECG data, as illustrated by the screen shots of FIGS. 3, 4, 7, 8, 9A, and 9B. FIGS. 3 illustrates a 12 lead, standard height standard width, with 12 leads at a time. FIG. 4 illustrates a 12 lead ECG in an alternate format showing 2–6 lead by 5 second lead groups as previously described. These displays may be used, for example, to determine an overall evaluation of the data. FIG. 7 illustrates a double-height double-width display of the same ECG displayed in FIG. 4.This display may be used to make detailed measurements. FIGS. 8, 9A, and 9B illustrate increasing magnification of the waveform data to provide increased marker placement precision. FIGS. 9A and 9B illustrate the option to display only a single lead of data. FIG. 9B illustrates the use of the ½ scale display option that may be used for large amplitude waveforms.

Figure 14:
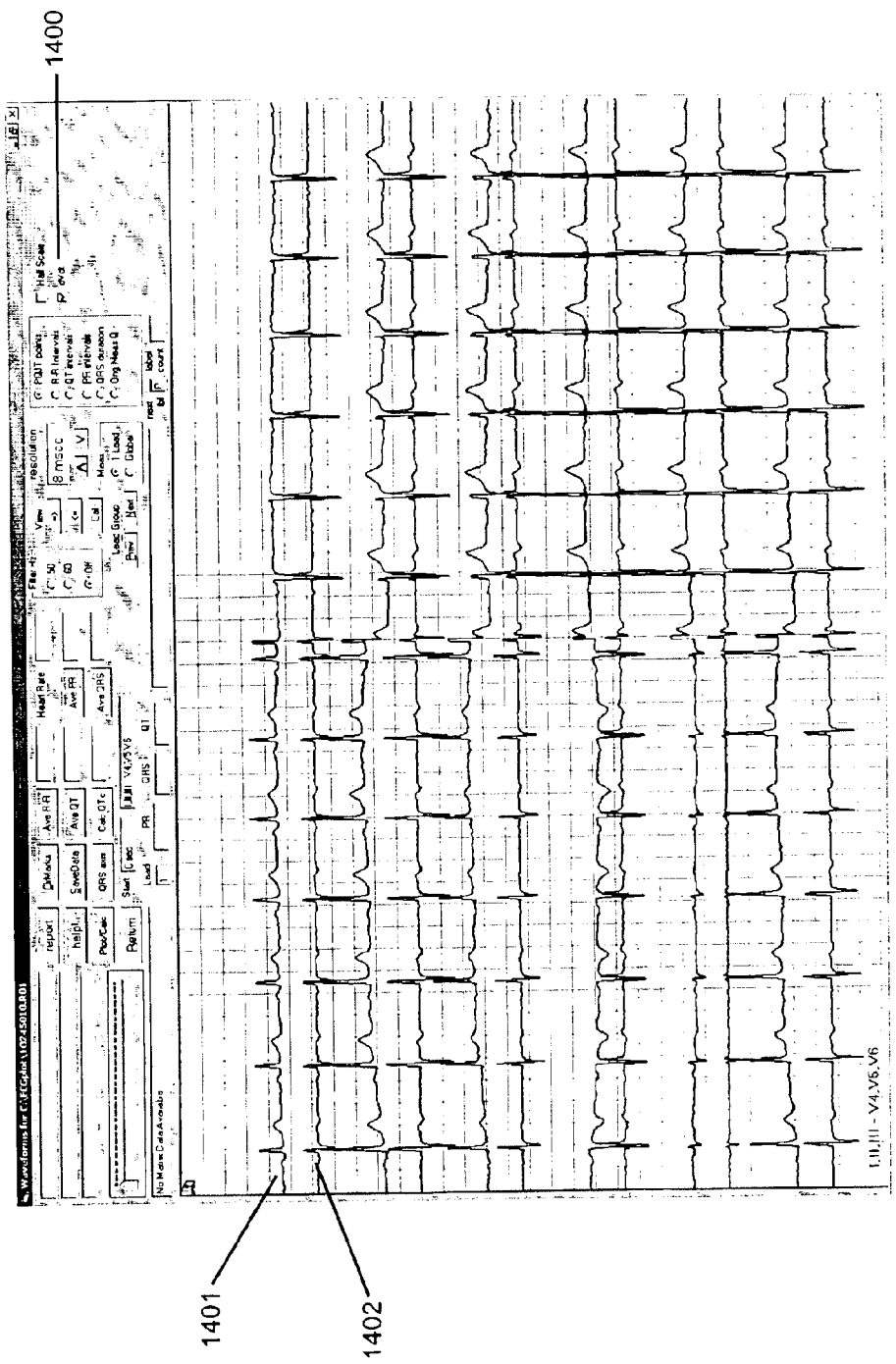
FIG. 14 is an illustrative display screen that shows an example of how derived data such as the time derivative of the time series waveform data may be presented with the original data to assist in the analysis of the data. This figure also illustrates an alternative method for the display of comparison time series waveform data may be displayed in accordance with the principles of the current invention.

FIG. 14 illustrates an additional method of displaying derived or calculated data in conjunction with the original time series data. In this figure, the first time derivative of the time series data 1402 is presented just below the original data 1401. Activation of this display option may be with the selection of a check box 1400, for example. The presentation of this data may be used to assist in the analysis of the original data by helping to determine where the maximum rate of change of the data occurs, for example. This same figure also illustrates how the time series data for a comparison waveform may be presented in close alignment with the original data for comparison as an alternative to the side by side comparison display illustrated in FIG. 6, for example.

Figure 15:
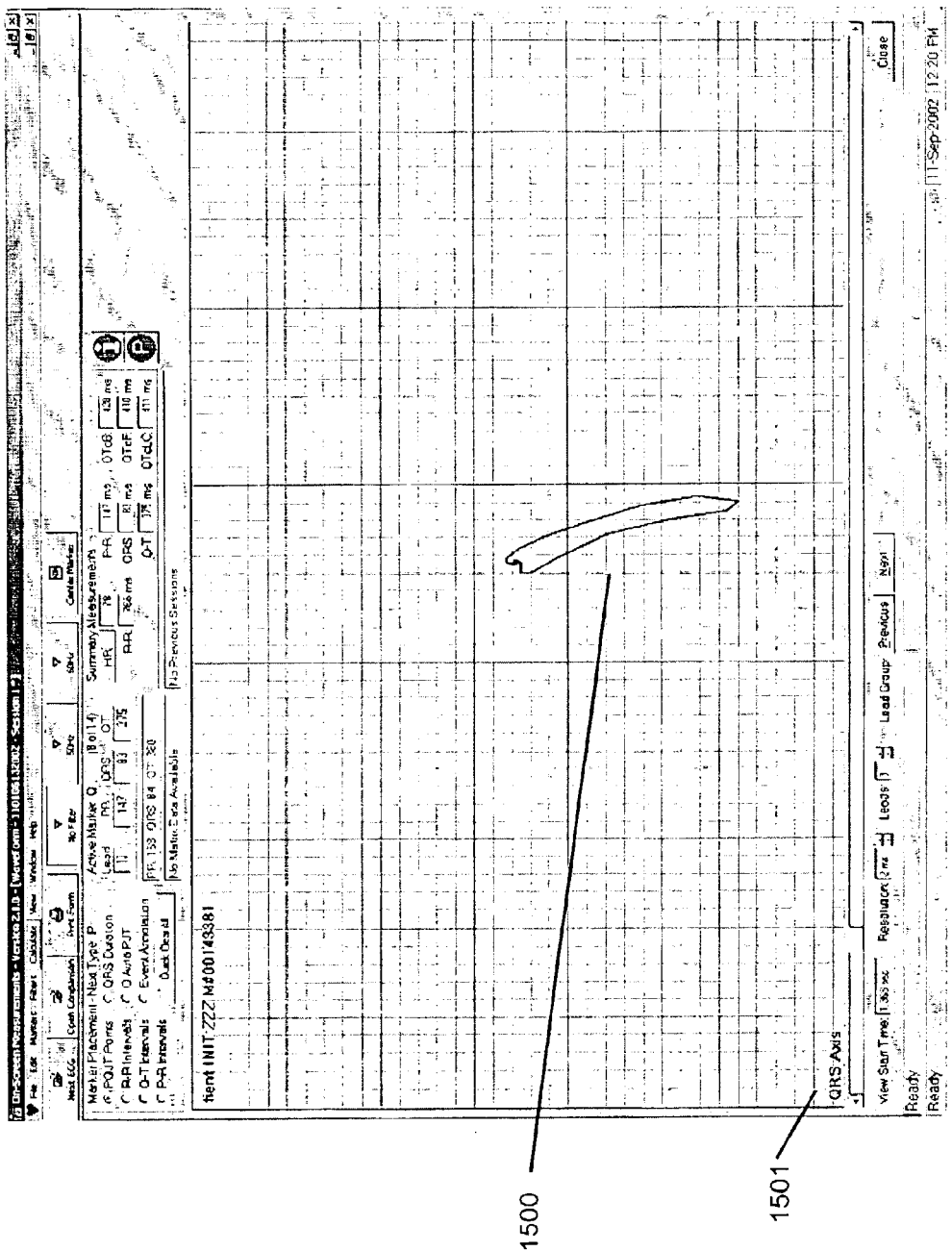
FIG. 15 is an illustrative display screen that shows an example of the menu that may be used to indicate acceptance of the edited report and enter instructions for subsequent processing in accordance with the principles of the present invention.
Figure 16:
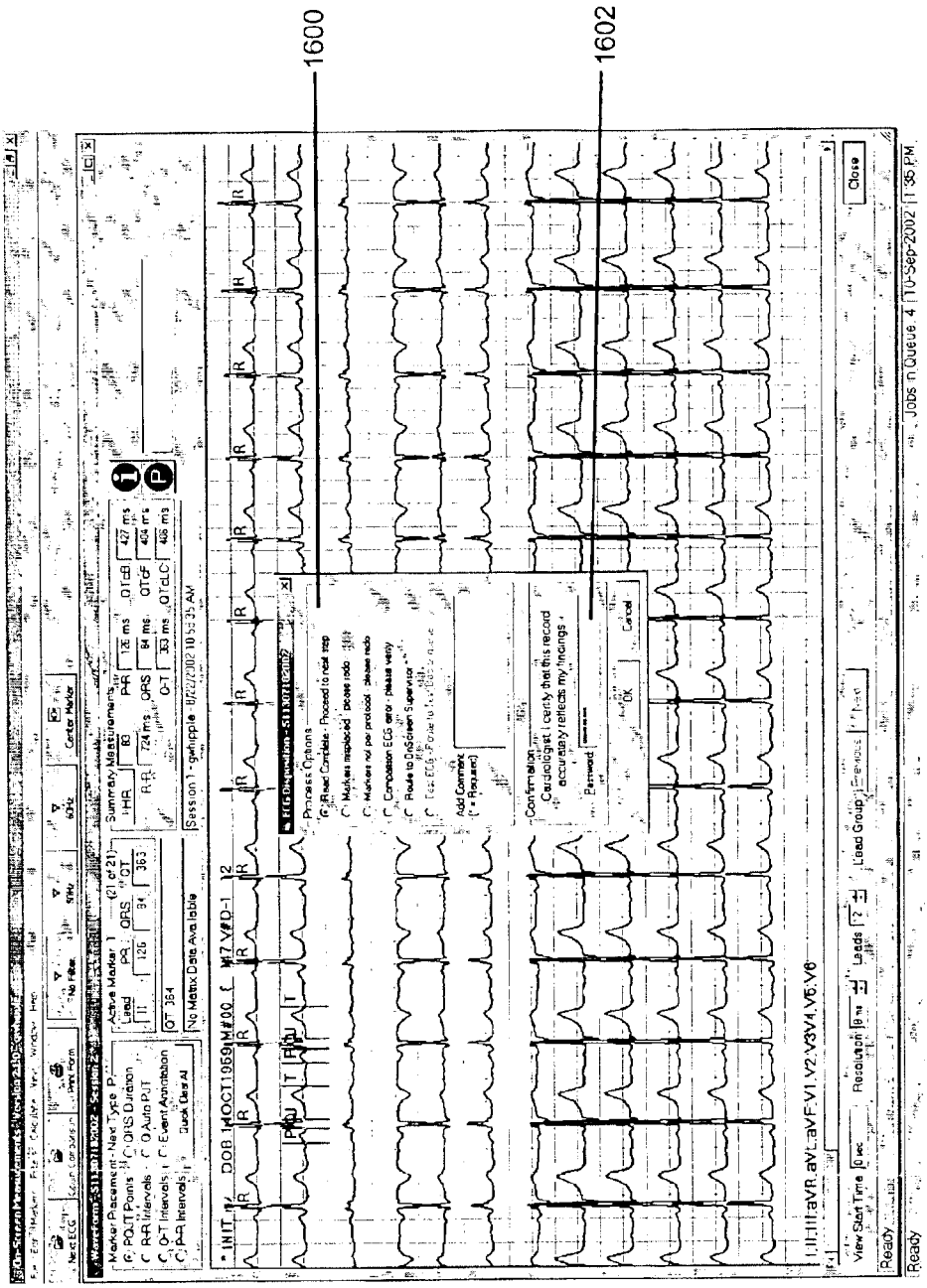
FIG. 16 is an illustrative display screen that shows an example of an exit screen that may be presented to a user when it has completed a review session.

FIG. 15 illustrates an additional method of the current invention for displaying the original time series data by plotting 2 or more sets of the time series data against each other rather than against time. As an illustrative example, the ECG lead values of lead I and lead aVF are plotted against each other 1500 to represent the frontal plane QRS axis loop. The plot results may be indicated with a label 1501 and activated by a selection from a drop down menu, for example. The resultant two dimensional vector plot of heart activity within the body assists a cardiologist in the analysis of a given ECG. FIG. 16 is an illustrative example of an exit screen that may be presented to a user when they have completed a review session. The process options 1600 allow the user to select the next step or allow processing to continue as required. The confirmation password 1602 requires the confirmation by the user of completion by entering their password.

Figure 17:
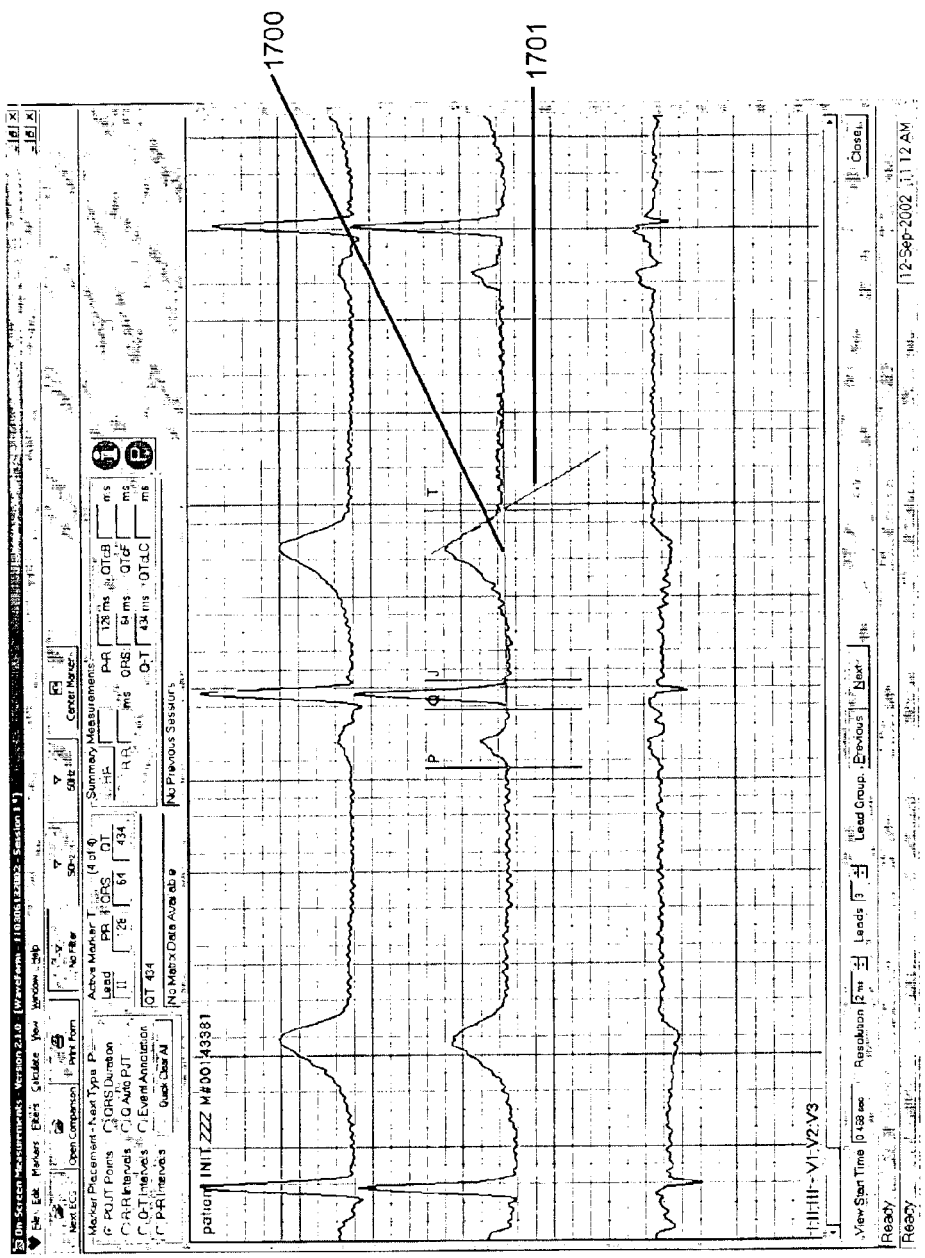
FIG. 17 is an illustrative display screen that shows that ancillary lines can be presented on a display with specific relationships.

As illustrated in FIG. 17, in response to user input or as a result of computer analysis, ancillary lines may be drawn on the display with specific relationships to the time series waveform to assist in the analysis of and marker placement on the time series data. These ancillary lines may take the form of placing an isoelectric line 1700 with relation to the time series data or the placement of a tangent line 1701 at a particular point on the data, for example.

In an illustrative embodiment a user initiates the operation of an interactive time-series data display in accordance with the principles of the present invention by a login process which may include security processes that permit different levels of access to different users. After logging in, the system provides access to time-series data for measurement. The time-series data, such as ECG data, may be stored and accessed though a database manager, for example, or the data may be provided to the interactive display "real time" by connection to an ECG machine. In a central processing embodiment, data is transmitted from one or more ECG machines to a central location for processing by one or more interactive display systems in accordance with the principles of the present invention.

An interactive display system in accordance with the principles of the present invention provides an on-screen measurement function that allows an operator, such as a cardiologist, to select one or more displayed points for the measurement of time-series data. The system captures, not only the coordinates of the selected points, but corresponding waveform coordinates, with a translation of the coordinates into "real world" values, in microvolts and milliseconds, for example. The system also logs a record of all selections and edits and identifies the parties responsible for the selections. In an illustrative embodiment, the interactive display system provides a report file and a measurement matrix file related to such measurements. The report file, measurement file, and associated transaction oriented data files may be individual files or may be configured as a set of database tables to contain all the required data related to the analysis and assessment of the original time series data.

An interactive display system in accordance with the principles of the present invention may be used in the measurement, annotation, and analysis of time-series data, such as ECG data. Various display formats may be employed, including those that emulate traditional strip-chart hard-copy reports. The use of such traditional formats builds upon the existing knowledge-base of those in the field, such as technicians and cardiologists, who have extensive training in the measurement, modeling, and analysis of such time-series records. The system may display data related to one or more channels, including time-series data from a standard twelve-lead ECG machine. Additional display formats, such as frequency domain representations and other derived or processed data, may also be employed and displayed.

In an ECG measurement embodiment, the interactive display may provide a variety of display modes, including twelve-lead resting, 60-second rhythm, 120-second, and longer rhythm displays. In a twelve-lead resting ECG, the leads may be plotted in a variety of display arrangements to optimize the information content of the display for the operator. Such arrangements may include display of simultaneously acquired data so that the time relationship of the different waveforms is maintained for analysis, as well as the ability to display data that is not simultaneously acquired either in its time sequence acquired format or in a more compact and understandable printed report format. Examples of these types of display have been previously mentioned as examples of printed report formats that the current invention emulates to take advantage of trained operator knowledge and experience.

In addition to waveform representations, the display may also provide for the display of additional information, such as a cardiologist's comments and reports, for example. Such information may be displayed in one or more separate "windows" located on the display, which windows may be opened or closed, re-sized, and re-positioned in response to user input. The interactive display may support measurements in a variety of dimensions, including those represented by horizontal and vertical display axes.

Time series data that is displayed by an interactive display in accordance with the principles of the present invention may be obtained from a variety of sources, including stored digitized ECG data, data representing scanned, digitized ECG paper records, or data received, directly or indirectly, and in some sense "live," from an ECG device. The system is capable of capturing multiple records from different subjects, along with relationships among the recordings. Time-series data such as may be displayed and measured through the use of an interactive display in accordance with the principles of the present invention may be organized generally so that recordings from a patient in a single sitting is referred to as a session, and recordings over a period where experimental conditions are static will be referred to herein as a session.

Continuous, evenly-sampled data from a set of channels may be referred to as an epoch. For example, in a twelve-lead ECG data obtained from six leads, followed by data from six other leads, the data is organized as two epochs of a single session. Data from a session may be organized in a packet that includes a header identifying the person from who the recording was obtained, what equipment was used, and when the recordings began. Each epoch may identify data collection characteristics, the characteristics of the channels, and annotations that apply across all channels. An epoch's data collection characteristics include when the data collection started relative to the session's baseline data and time and the sample rate for data on each channel, for example. Channel characteristics may include the number of bits, zero-offset, units and scale factor by which data is to be multiplied for conversion to given units. Filtering information, such as characteristics of bandpass, highpass, and lowpass, for example, may also be included.

Annotations at the session level can be used to indicate such events as when study procedures were performed relative to the recording session. Annotations at the epoch level may be used to mark features visible in the data for multiple channels, e.g., PVCs or periods of A-V block. Annotations at the channel level would typically be used to mark events specific to that channel's data, for example, the beginning of the P wave. Each annotation may characterize a particular time point, denote the beginning and end of an interval, or may be associated with where a particular amplitude measurement is made. An interactive display in accordance with the principles of the present invention may support any of the following ECG-related measurements: duration of all or a selected part of a phase of the cardiac cycle, the amplitude of particular features in a cardiac cycle (absolute value or with respect to a reference iso-electric line or point), and the duration or presence of periods of particular interest where notable events are taking place. Special measurements may include a requirement to determine a minimum or certain number of annotation points in a certain specified lead or leads so that particular protocol requirements can be met. The current invention may be able to provide a display of these requirements to facilitate the efficient processing of these requirements.

The new interactive display may produce a report that includes: a digitized twelve-lead ECG waveform, patient demographics, and the measurements and findings that are related to the analysis of the test. Additionally, the interactive display may, in response to a user prompt or as a default, produce and display reduced data. For example, the display may determine and display the average heart rate during a test, the longest PR interval associated with any lead, the longest QRS duration from any lead, or the longest QT interval from any lead. Additionally, the display system may produce and/or display the rate corrected QT interval based on the QT and the average heart rate—using a selectable conversion methodology, or the frontal plane QRS axis determined from combinations of the limb leads. The interactive display system supports study-specific special measurements, such as determination of the location of the maximum slope of a particular waveform feature by calculating the time derivative of the original signal.

As described in relation to FIGS. 10 and 11, for example, the system may also provide for the display of interpretation codes and statements. Such codes and statements may be automatically generated, using expert system, neural network, or other analysis systems, and may be displayed in one or more "windows" within the display. Such windows may be fixed in position, size and other attributes or an operator may resize, relocate, or otherwise alter the window for viewing or comparison purposes. The interpretation codes and/or statements may indicate a note worthy or abnormal ECG feature or finding, and may include an overall assessment code, for example. The system may also provide for the display of additional interpretive comments that may be entered, for example, by a reviewing cardiologist. Additionally, an overall assessment code, a comparison statement, test identification, summary measurements and interpretations may be displayed in a separate text area. Reports of abnormalities may be the result of computer interpretation, with cardiologist review. The system may also check the entered interpretation codes and comments for consistency with the measurements generated by the annotated data and with each other. This validity checking is provided as guidance to the operator concerning agreed to standards. The system may also provide additional checking to verify that all required special measurements have been completed prior to closing a session.

In an illustrative embodiment, a report file explicitly captures the data structure of a recording session, epochs comprising data acquired over the same interval, and representations of data obtained during an epoch. The system may include a mechanism to annotate points in the time and intervals corresponding to single channels, representations, and sessions. Each report file may include a single unique identifier created for each recording, which provides for an unambiguous link between each recording and other data stored for a particular test in a study.

Pre-set marker information may be extracted from the report file or the measurement matrix file and used to assist the technician in the initial placement of the markers. Results of each markup session are stored in the database. Each time an ECG is reviewed, the most recent set of marker data will be used to pre-set the markers. The data from a cardiologist's measurements and interpretation will be stored as part of the final report concerning the set of data being processed.

The system will use the locations of specifically annotated data points to derive or calculate values to be included in the report. Based on standard electrocardiographic practice or special instructions for a particular test, the operator will annotate the required points. All such points that contribute to the analysis and interpretation of the ECG may be included. The location of the annotated points are with reference to the beginning of the data for that lead and must include the lead identification for the lead being measured in addition to the identification label for the point. The invention will support the inclusion of annotation points in addition to those often used in standard analysis of ECGs. In an illustrative embodiment, the intervals are derived from the indicated data points and will not require a separate entry. PR, QRS, QT. All intervals may not be available for all leads. Data will only be recorded for those leads in which the intervals were marked.

In accordance with the principles of the present invention, the system is able to annotate the presence of particular events of interest, including: Premature beats (by type) to include PVC's, PAC's, Ventricular Tachycardia, for example. An interactive display system in accordance with the principles of the present invention provides a resolution of at least the sample period of the source data to determine the location of the points and intervals. Higher resolution may also be provided to allow estimates or calculations of annotation points to be made between actual sample values. Measurements may be made across more than one lead for ECGs that contain synchronous (simultaneously acquired) data. These measurements are classified as global in nature and may be used to help identify longest and shortest intervals for a set of leads.

Calculations may be made by the system for the intervals as the interval end points are indicated. The measurements will be updated each time one of the markers involved in a measurement is moved. Measurements for the selected beat and for the average of the beats in the selected lead will be updated as markers are placed or moved. Calculations may be made for the following intervals. Leads without indicated points will not be included in the calculation of the intervals.

PR interval—P onset to QRS onset, QRS duration—Q (QRS) onset to J point (QRS end), QT—Q onset to T end, Heart Rate—based on the average of consecutive R peaks that are selected in a lead, and QTc—this value will use the QT interval and the average R to R interval to determine the QTc value. Options for the generation of the QTc value will be the use of the Bazeft formula (square root correction), Fredericia formula (cube root correction), the formula using the 2.5 root correction or linear correction, or other formulae that may be required for rate correction of the QT interval. The minimum and maximum heart rate will also be recorded to allow the display of the rate range information.

In the present invention a variety of statistical methods may be used to combine the individually determined measurements to determine a representative value for the measurement as the summary value for the test. In an illustrative embodiment, if more than one interval is determined in a particular lead, then the average of the values in a lead will be used as the value for that lead. If more than one lead contains values for a particular measurement, then the maximum value for all the leads may be used.

Special measurements may be processed manually or with computational support. In an illustrative embodiment, support for these measurements is made available by making the database tables to which these values must be entered available to the on-screen measurements program to read. Additionally, the system allows an operator to read from study-specific special measurements table, the labeling requirements, the database, table, field, and format. In an illustrative embodiment, undesignated labels are available to allow making special measurements and annotations. The labels and the associated database, table, field, and format information with the instructions for making the measurements may be automatically or manually loaded based on information provided with the test. These labels will be used to identify the measurement or event marks in the same way as the standard data points and intervals are identified. The instructions for a particular measurement will be available under the general help function or will be displayed when that special measurement mark is selected and the Help button is pressed. This allows operators who are familiar with the measurement to not have screen space taken up with the instructions.

As previously described, the system supports viewing comparison ECGs. An operator may select a comparison ECG (when one or more comparisons are available) and view the associated report text and waveforms. The user may not make any changes to the comparison ECG. The ECG report text will not be updated with the results of the processing. The details of what was changed, when it was changed, and who made the changes will be recorded in a database as part of the tracking of processing of the test. In an illustrative embodiment, the session records and results file records are an integral part of the database and are available to be exported.

Output to database tables may include the output from the measurement markup portion of the interactive display engine, including all measurement points with the label for each point or interval, the lead in which the measurement was made, the location of the point, in milliseconds, from the beginning of the lead, and the end point, in milliseconds, for an interval. For global measurement points or intervals, the lead designation will designate the lead group with which the markers are related. Also included in the database is the login ID of the person making the changes. Current changes will not obscure the record of previous changes made to the file. All changes, including changes back to original values will be retained. The options and settings that were used during the changes, including the maximum magnification used, the waveform plot and marker line widths (final settings), and the marker color set will be recorded. The following items will also be recorded: the date and time when the session was begun and when it ended, the lead length of each lead and the offset from the earliest lead, (a zero entry would indicate that no offset is present and the lead so indicated is synchronous with the other lead with an offset of 0), whether a filter was used, and the type of filter, if the data was filtered. This information may be supplied in different ways depending on the procedures used to process the test.

A software implementation of the above described embodiment(s) may comprise a series of computer instructions either fixed on a tangible medium, such as a computer readable media, e.g. diskette, CD-ROM, ROM, or fixed disc, or transmittable to a computer system, via a modem or other interface device, such as communications adapter connected to the network over a medium. Medium can be either a tangible medium, including but not limited to, digital or analog communications lines, or may be implemented with wireless techniques, including but not limited to microwave, infrared or other transmission techniques. The series of computer instructions embodies all or part of the functionality previously described herein with respect to the invention. Those skilled in the art will appreciate that such computer instructions can be written in a number of programming languages for use with many computer architectures or operating systems. Further, such instructions may be stored using any memory technology, present or future, including, but not limited to, semiconductor, magnetic, optical or other memory devices, or transmitted using any communications technology, present or future, including but not limited to optical, infrared, microwave, or other transmission technologies. It is contemplated that such a computer program product may be distributed as a removable media with accompanying printed or electronic documentation, e.g., shrink wrapped software, preloaded with a computer system, e.g., on system ROM or fixed disc, or distributed from a server or electronic bulletin board over a network, e.g., the Internet or World Wide Web.

Although various exemplary embodiments of the invention have been disclosed, it will be apparent to those skilled in the art that various changes and modifications can be made which will achieve some of the advantages of the invention without departing from the spirit and scope of the invention. It will be apparent to those reasonably skilled in the art that other components performing the same functions may be suitably substituted. Further, the methods of the invention may be achieved in either all software implementations, using the appropriate object or processor instructions, or in hybrid implementations that utilize a combination of hardware logic, software logic and/or firmware to achieve the same results. Processes illustrated through the use of flow charts may not be strictly linear processes and alternative flows may be implemented within the scope of the invention. The specific configuration of logic and/or instructions utilized to achieve a particular function, as well as other modifications to the inventive concept are intended to be covered by the appended claims.

The foregoing description of specific embodiments of the invention has been presented for the purposes of illustration and description. It is not intended to be exhaustive or to limit the invention to the precise forms disclosed, and many modifications and variations are possible in light of the above teachings. The embodiments were chosen and described to best explain the principles of the invention and its practical application, and to thereby enable others skilled in the art to best utilize the invention. It is intended that the scope of the invention be limited only by the claims appended hereto.

What is claimed is:

1. A method of marking time-series medical data that are graphically displayed in the form of a set of waveform traces on a display monitor, each trace embodying a plurality of features, the method comprising the steps of:
   A. manually identifying a location of at least one feature of a first trace;
   B. displaying on the monitor in relation to the identified first trace feature location at least one marker;
   C. displaying on the monitor at least one label corresponding to the marker and the trace feature; and
   D. automatically displaying on the monitor markers and labels associated with the one feature on subsequent waveform traces.

2. The method of claim 1 wherein the time series medical data is electrocardiogram (ECG) data and and step A comprises indicating a type of ECG sequence for which a trace feature is to be located.

3. The method of claim 2, wherein said type of sequence is a PQJT sequence.

4. The method of claim 3, wherein step C comprises displaying a label "P" in proximity to a corresponding first marker in the PQJT sequence.

5. The method of claim 2, wherein step A comprises inputting data to a graphical user interface.

6. The method of claim 2, wherein said type of seuence is a QPJT sequence.

7. The method of claim 6, wherein step C comprises displaying a label "Q" in proximity to a corresponding first marker in the QPJT sequence.

8. The method of claim 2, wherein step A comprises indicating that a QRS onset sequence is to be labeled.

9. The method of claim 8, wherein step C comprises displaying a Q onset label in proximity to a corresponding first marker in the QRS onset sequence.

10. The method of claim 9, further comprising the steps of:
    displaying on the monitor a second marker in relation to a P onset; and
    displaying a P onset label corresponding to the second marker.

11. The method of claim 1, further comprising the step of displaying a reference line between the at least one marker and the label.

12. The method of claim 1 further comprising the step of displaying the time series medical data as a waveform trace superimposed on a gridded background.

13. A method of marking time-series electrocardiogram (ECG) data comprising the steps of:
    A. displaying on a display monitor the time series ECG data as a waveform trace superimposed on a gridded background;
    B. accepting user input that indicates a type of (ECG) sequence for which a feature is to be located;
    C. locating a displayed trace feature of the indicated ECG sequence on the monitor;
    D. in response to said user input, placing a first marker on the displayed waveform trace in relation to the located displayed trace feature;
    E. displaying a label on the displayed waveform trace that identifies the first marker; and
    F. automatically displaying on the monitor markers and labels associated with the one feature on subsequent waveform traces.

14. The method of claim 13 further comprising the step of displaying the gridded background as rectangular cells that delimit 40 millisecond by 0.1 millivolt sections of gridspace and displaying a set of super-cells that each delimit 200 milliseconds by 0.5 millivolts of grid-space.

15. An apparatus for marking time-series medical comprising:
    A. a display;
    B. a graphical user interface; and
    C. a controller coupled to the display and graphical user interface, said controller configured to:
       1) render on the display the medical time-series data as at least one trace embodying a set of trace features;
       2) locate a displayed medical trace feature;
       3) place a first marker related to the displayed medical trace feature on the display;
       4) place a label on the display that identifies the placed first marker; and
       5) automatically display markers and labels that correspond to the displayed medical trace feature on subsequent medical traces.

16. The apparatus of claim 15, wherein the controller is further configured to accept a user input that indicates a type of electrocardiogram (ECG) sequence for which a feature is to be located.

17. The apparatus of claim 16, wherein the controller is further configured to accept an input from a user, the input indicating that a PQJT sequence is to be labeled.

18. The apparatus of claim 16, wherein the controller is further configured to accept an input from a user, the input indicating that a QPJT sequence is to be labeled.

19. The apparatus of claim 16 wherein the controller is further configured to accept a user input that indicates that a QRS onset is to be labeled.

20. The apparatus of claim 15, wherein the controller is further configured to accept a user input from the graphical user interface.

21. The apparatus of claim 15, wherein the controller is configured to display time series medical data as a trace superimposed on a gridded background.

22. An apparatus for marking time-series medical data comprising:
    A. a display;
    B. a graphieal user interface; and
    C. a controller counled to the display and graphical user interface, said controller configured to:
       1) display time series medical data as at least one trace embodying a set of trace features superimposed on a gridded background;
       2) accept user input that indicates a type of electrocardiogram (ECG) sequence for which a feature is to be located;
       3) locate a displayed medical trace feature;
       4) place a first marker on the display related to the displayed medical trace feature;
       5) place a label on the display that identifies the placed first marker; and
       6) automatically display markers and labels that correspond to the displayed medical trace feature on subsequent medical traces.

23. The apparatus of claim 22, wherein the controller is further configured to display the gridded background as rectangular cells that delimit 40 millisecond by 0.1 millivolt sections of grid-space and to display a set of super-cells that each delimit 200 milliseconds by 0.5 millivolts of grid-space.

24. A method for generating a plurality of markers identifying features of time-series medical data that are graphically displayed in the form of a set of waveform traces on a display monitor, to facilitate analysis of the waveform data, the method comprising the steps of:

selecting a feature marker sequence that either requires:
A. manual placement of all feature points to be marked;
B. manual placement of an initial marker point and automatic
placement of the remaining marker points;
interactively placing the markers on the displayed waveform traces, in the sequence selected in the selecting step, on one or more of the waveform traces; and
in response to placement of each marker in the selected sequence, automatically generating a label associated with the sequence and displaying the generated label in the vicinity of the associated mark on the displayed waveform.

25. A method as recited in claim 24, wherein the time series medical data are electrocardiogram (ECG) data, and further comprising the step of:

interactively adjusting the location of the marker on the display in accordance with operator identification of certain patterns in the ECG.

26. A method as recited in claim 25, wherein the selecting step comprises selecting a sequence that requires manual placement of an initial marker point and automatic placement of the remaining marker points, and further comprises:

adjusting the location on the display of the initial marker point following initial placement thereof.

27. A method as recited in claim 26, wherein the automatic placement of remaining marker points is based on precalculated interval measurement data.

28. A method as recited in claim 26, wherein the initial marker point corresponds to a QRS onset point of a portion of the ECG data and the remaining marker points corresponding to a P wave onset point, the QRS end point and a T wave end point of the ECG portion.

29. A method as recited in claim 28, further comprising automatically placing markers and associated labels in subsequent displayed portions of the ECG data, corresponding to previous marker features.

30. A method as recited in claim 28, wherein the ECG waveform data is displayed on an interactive display superimposed on a millimeter grid background.

31. A method as recited in claim 30, further comprising the step of automatically responding to operator input to magnify the waveform and grid background maintaining the aspect ratio and size relationships of the waveform and the grid.

32. A method as recited in claim 30, wherein movement of the markers in response to operator input are moved in pixel increments corresponding to a time increment represented by the pixel size on the waveform display.

33. An apparatus for interactively marking time-series medical data comprising:

a graphical display;
a storage device;
an interactive operator input pointing device; and
a controller coupled to the graphical display, the storage device, and the interactive operator input device, the controller configured to:
render the time-series data to display at least one waveform tracing that embodies a set of trace features,
respond to operator input to select a specific marker sequence,
respond to the pointing device to indicate the location of features on the display and to place a marker on the waveform based on a location indicated by the pointing device,
automatically place a label with the marker, the label corresponding to the next marker in the selected sequence to be placed,
respond to operator input to adjust the marker location, and
respond to additional operator input to manually or automatically place additional markers based on a selected marker sequence.

34. Apparatus as recited in claim 33, wherein the time-series medical data is electrocardiogram (ECG) data, and the selected marker sequence comprises:

an initial marker in the sequence placed in accordance with manual input and the remaining markers in the sequence placed automatically based on data read in by the controller or stored in the controller as a result of previously placed marker sets.

35. Apparatus as recited in claim 34, wherein the locations and labels of the markers correspond to calculated ECG waveform intervals, calculated interval values being automatically updated when any of the associated markers are moved.

* * * * *